US010206809B1

(12) United States Patent
Goldberg

(10) Patent No.: US 10,206,809 B1
(45) Date of Patent: Feb. 19, 2019

(54) TONGUE EMBRACING ORAL MEMBER RETENTION DEVICE

(71) Applicant: Howell Goldberg, Parkland, FL (US)

(72) Inventor: Howell Goldberg, Parkland, FL (US)

( * ) Notice: Subject to any disclaimer, the term of this patent is extended or adjusted under 35 U.S.C. 154(b) by 634 days.

(21) Appl. No.: 14/703,858

(22) Filed: May 4, 2015

Related U.S. Application Data

(63) Continuation-in-part of application No. 13/609,754, filed on Sep. 11, 2012, now abandoned, which is a continuation-in-part of application No. 12/883,156, filed on Sep. 15, 2010, now Pat. No. 8,261,748.

(51) Int. Cl.
  *A61F 5/56* (2006.01)
  *A61F 5/37* (2006.01)
  *A61C 5/14* (2006.01)
  *A61C 5/90* (2017.01)
  *A61C 7/08* (2006.01)

(52) U.S. Cl.
  CPC .............. *A61F 5/566* (2013.01); *A61C 5/14* (2013.01); *A61F 5/37* (2013.01); *A61F 5/56* (2013.01); *A61C 5/90* (2017.02); *A61C 7/08* (2013.01)

(58) Field of Classification Search
  CPC ... A61F 5/56; A61F 5/566; A61C 7/08; A61C 5/90
  USPC ....................... 128/848, 859, 860; 433/6, 140
  See application file for complete search history.

(56) References Cited

U.S. PATENT DOCUMENTS

| | | | |
|---|---|---|---|
| 4,169,473 A | 10/1979 | Samelson | |
| 5,318,043 A | 6/1994 | Burr et al. | |
| 5,649,540 A | 7/1997 | Alvarez et al. | |
| 5,921,241 A * | 7/1999 | Belfer | A61F 5/566 |
| | | | 128/848 |
| 6,422,243 B1 | 7/2002 | Daram | |
| 6,877,513 B2 | 4/2005 | Scarberry et al. | |
| 7,607,439 B2 | 10/2009 | Li | |
| 8,037,886 B2 | 10/2011 | Solos et al. | |
| 2003/0234022 A1* | 12/2003 | Belfer | A61F 5/566 |
| | | | 128/861 |
| 2010/0154802 A1 | 6/2010 | Fuselier | |

* cited by examiner

*Primary Examiner* — Keri J Nelson
(74) *Attorney, Agent, or Firm* — Allen D. Hertz, P. A.; Allen D. Hertz

(57) ABSTRACT

An embracing attachment member or sheath and a maxilla attachment subassembly for retaining at least one of a patient's tongue and lip in a desired position. A sheath interlock member extends upward from a dorsal side of a sheath. A tongue receiving cavity is formed within the sheath for insertion and attachment to the patient's tongue. An interlock member is integrated into an accessory for attachment to the sheath interlock member. The accessory can be used to treat sleep apnea, restrain a patient's tongue in a desired position, restrain a patient's upper or lower lip in a desired position, and the like. The interlock design includes a wedge and a retention member that engages with the wedge. The retention member and wedge compress friction surfaces against one another, retaining the sheath interlock and the accessory interlock in a fixed position respective to one another.

23 Claims, 19 Drawing Sheets

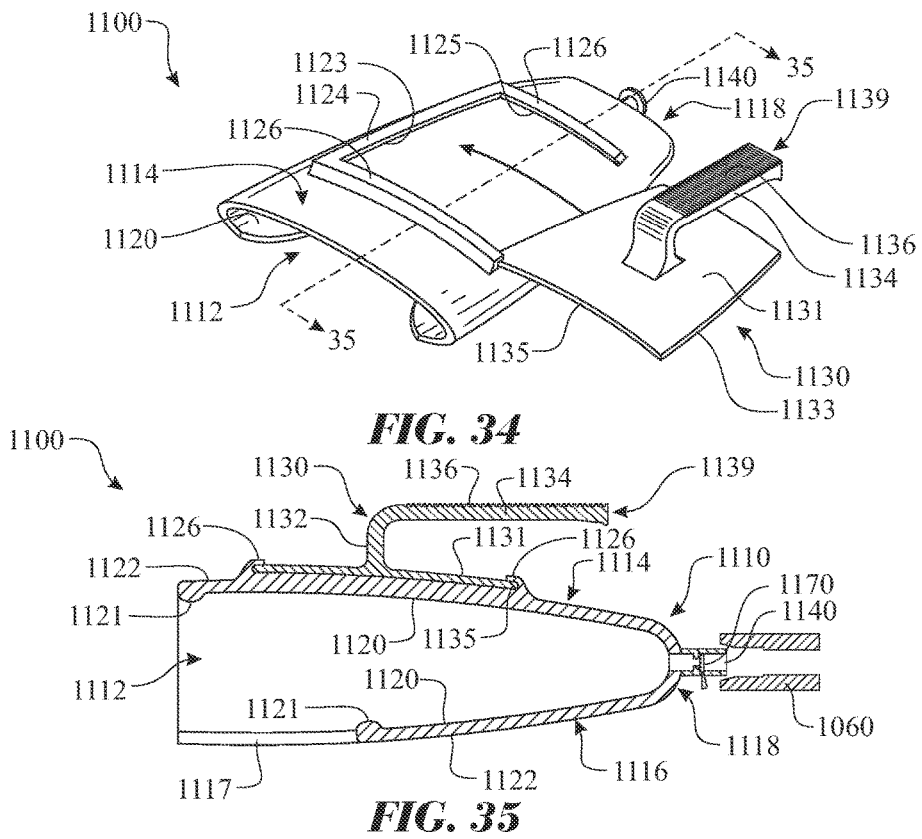
FIG. 34
FIG. 35
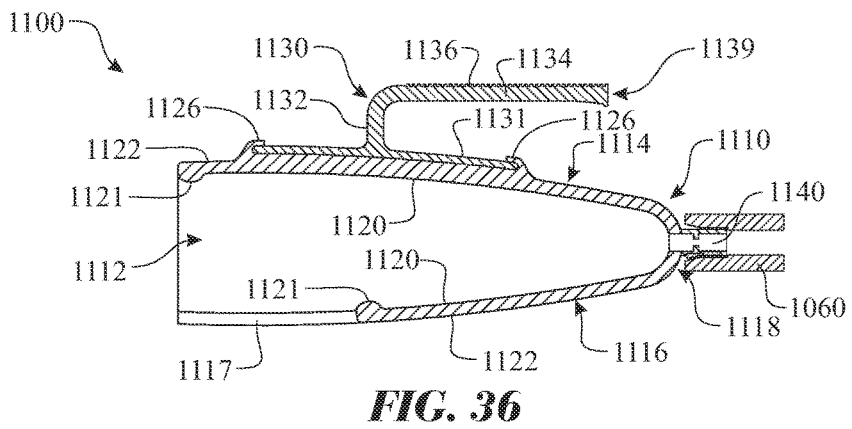
FIG. 36

TONGUE EMBRACING ORAL MEMBER RETENTION DEVICE

CROSS-REFERENCE TO RELATED APPLICATION

This Non-Provisional Utility Patent Application is a Continuation-In-Part (CIP) claiming the benefit of co-pending U.S. Non-Provisional Utility patent application Ser. No. 13/609,754 filed on Sep. 11, 2012, which is a Continuation-In-Part (CIP) claiming the benefit of U.S. Non-Provisional patent application Ser. No. 12/883,156, filed on Sep. 15, 2010 (Now Issued as U.S. Pat. No. 8,261,748 on Sep. 11, 2012), which are all incorporated herein in their entireties.

FIELD OF THE INVENTION

The present disclosure relates to an oral medical apparatus used for multiple purposes. More particularly, the oral medical apparatus comprises an attachment feature carried by a tongue engaging sheath. Any of a variety of accessories is supported by the attachment feature, wherein each accessory provides a function such as prevention of snoring and sleep apnea, retention of an upper or lower lip, positioning of a tongue, and the like.

BACKGROUND OF THE INVENTION

The present invention provides an oral medical apparatus used in the prevention of snoring and sleep apnea. Snoring is the vibration of respiratory structures and the resulting sound due to obstructed air movement when a human breathes during sleep. Generally, the uvula and soft palate are the anatomical structures that cause the sound of snoring if a human's tongue drops to the back of their mouth during sleep.

Sleep apnea is a sleep disorder characterized by having one or more pauses in breathing, or shallow breaths during sleep, and is typically accompanied by snoring. Each pause or cessation is generally referred to as an apnea, and can last from a few seconds to minutes. Additionally, each apnea may occur from five to thirty or more times per hour of sleep. Although most humans do experience some level of sleep apnea during their lifetime, a relatively smaller percentage (approximately 20%) of humans, suffer with chronic, severe sleep apnea. A combination of factors causes sleep apnea or snoring. One factor is the relaxation of muscle tone that results from sleep. Another factor is the vibration of soft, collapsible tissue surrounding the human airway, which causes snoring.

There are several snoring control devices known in the art. These devices provide for reception of the tongue in a hollow tongue-retained holder. One problem presented by these devices, however, is the inadequate fit between the tongue-retained holder and the user's tongue. In particular, the device determines the position of the tongue. Consequently, a relatively long tongue is not properly or comfortably accommodated within the socket. Different sized devices or custom fabricated devices can be provided to help overcome this shortcoming, wherein the variety and custom fit devices are provided at a higher cost.

Another known device provides a tongue sleeve configured for reception and retention of the outer extent of the user's tongue, and includes a shield shaped to be received and retained outside of the user's lip, as well as a component that allows the user to attach and adjust the shield to the tongue sleeve. This component permits for selective adjustment of the shield's position relative to the tongue, reducing snoring and airway obstruction.

Another device, known as the aveoTSD, provides suction between the device and the user's tongue. This suction prevents the tongue from moving toward the back of the mouth, thereby, keeping the airway open during sleep to prevent snoring. This device is known to slip and some wearer's have felt that it is uncomfortable.

During a dental or other oral medical procedure, it is desirous to retain the patient's lip and/or tongue in a desired position.

Unfortunately, with all of the attempted improvements that have been made in sleep apnea prevention devices, there remains a need for a device that is more comfortable to wear and provides more effective results.

Additionally, there are benefits to creating a series of accessories for a variety of applications based upon the use of a tongue embracing member.

SUMMARY OF THE INVENTION

The present disclosure is generally directed to a sleep apnea control device, the device comprising:
  a tongue attachment subassembly comprising:
  a sheath shaped to conform to a surface of an individual's tongue, the sheath having a tongue receiving cavity defining an opening for receiving the individual's tongue provided at a proximal end thereof, the sheath having an orientation defined by a dorsal side and a ventral side, and
  a sheath interlock member extending outward from the dorsal side of the sheath; and
  a maxilla attachment subassembly comprising:
  a maxilla tray shaped to conform to and removably engage with an individual's upper dental arch, the maxilla tray defined having an engagement side and an interlock side, and
  a tray interlock member extending from the interlock side of the maxilla tray and positioned to interlock with the sheath interlock member, which, when interlocked, extends an individual's tongue during use.

In one aspect, the sheath interlock member is fabricated of a rigid material and the tongue attachment subassembly is fabricated of a pliant material.

In another aspect, the device further includes an air extraction system. An embodiment of the air extraction assembly is provided, which comprises an air extraction valve integrated into the tongue attachment subassembly, wherein the valve is in fluid communication with the tongue receiving cavity. The air extraction device may include an air extraction pipette in fluid communication with an air extraction bulb, where the air extraction pipette is in fluid communication with the air extraction valve to remove air from within the tongue receiving cavity. The air extraction device can be retained or integrated with the air extraction valve or removable therefrom.

In yet another aspect, the sheath interlock member further comprises a sheath interlock ridge, and the tray interlock member further comprises a tray interlock ridge, the ridge having an interlock interface to removably engage the sheath interlock ridge and the tray interlock ridge.

In yet another aspect, the interlock interface is fabricated having a series of teeth and teeth-receiving receptacles.

In yet another aspect, the interlock teeth are disposed at an acute angle.

In yet another aspect, the tongue attachment subassembly further includes a tongue base clearance defined by a U-shaped recession in the ventral side, which extends inward from an opening of the tongue receiving cavity opening.

In yet another aspect, the tongue attachment subassembly is fabricated having a bladder formed within the main body walls, wherein the air extraction valve is provided in fluid communication with the bladder. The user extracts air from the bladder, securing the tongue attachment subassembly to the individual's tongue.

In yet another aspect, the sheath interlock member further comprises a sheath interlock array, and the tray interlock member further comprises a tray interlock array, wherein the sheath interlock array and the tray interlock array removably engage with one another in a manner enabling both lateral and longitudinal adjustments. In a preferred embodiment, the arrays comprise a series of interlocking pins and pin receiving cavities.

In a second embodiment, the present disclosure further comprises an accessory to be adapted to the tongue attachment subassembly to create a lip positioning appliance, the appliance comprising:
 a tongue attachment subassembly comprising:
 a sheath shaped to conform to a surface of an individual's tongue, the sheath having a tongue receiving cavity defining an opening for receiving the individual's tongue provided at a proximal end thereof, the sheath having an orientation defined by a dorsal side and a ventral side, and
 a sheath interlock member extending outward from the dorsal side of the sheath; and
 a maxilla lip retention subassembly comprising:
 a lip retention section having an arched shape to follow a contour of a patient's lip,
 a maxilla lip retention positioning arm extending from the lip retention section,
 a tray interlock member located at an attachment end of the maxilla lip retention positioning arm and located to interlock with the sheath interlock member,
 wherein when interlocked and installed, retains the lip retention section in engagement with an individual's lip, and
 a tray interlock member extending from the interlock side of the maxilla tray and positioned to interlock with the sheath interlock member, which, when interlocked, extends an individual's tongue during use.

In one aspect, the sheath interlock member can be adapted to a maxilla lip retention subassembly to retain a patient's maxilla lip and tongue in a desired position during a procedure.

In another aspect, the sheath interlock member and maxilla lip retention subassembly further comprising a longitudinally adjusting interface between the two members.

In yet another aspect, the sheath interlock member and maxilla lip retention subassembly further comprising a longitudinally adjusting interface between the two members. The longitudinal adjustment can be used to control the position of the patient's tongue during a procedure.

In yet another aspect, the sheath interlock member and maxilla lip retention subassembly the longitudinally adjusting interface between the two members is provided by a series of interconnecting elements. The feature can introduce lateral adjustments with a laterally arranged series of interconnecting elements.

In yet another aspect, the sheath interlock member and maxilla lip retention subassembly the longitudinally adjusting interface between the two members is provided by a series of pins and mating series of receptacles.

In yet another aspect, the sheath interlock member and maxilla lip retention subassembly the longitudinally adjusting interface between the two members is provided by a slideably engaging interface.

In yet another aspect, the sheath interlock member and maxilla lip retention subassembly the longitudinally adjusting interface between the two members is provided by slideably engaging interface comprising a rail slideably engaging with a mating channel. The engagement can include a locking mechanism to retain the rail in a longitudinal relation with the mating channel.

In yet another aspect, the sheath interlock member and maxilla lip retention subassembly the longitudinally adjusting interface between the two members is provided by slideably engaging interface comprising a first arm in slideable communication with a second arm. The two arms can be retained to one another using any inter-arm retaining feature. The inter-arm retaining feature can be integrated into either arm or provided as a separate component.

In yet another aspect, at least one of the sheath interlock member arm and maxilla lip retention subassembly arm can include a position locking feature, wherein the position locking feature can be a series of ridges, teeth, scalloping, and the like. The position locking feature would engage with a position retaining member to retain the axial position relation between the sheath interlock member arm and maxilla lip retention subassembly arm.

In yet another aspect, the sheath interlock member arm and maxilla lip retention subassembly arm can are provided in a parallel relationship with a primary plane of the tongue attachment subassembly bladder.

In yet another aspect, a sheath interlock member arm of the sheath interlock member is fabricated of a substantially rigid material, whereas the tongue embracing member is fabricated of a material having substantially elastic properties.

In yet another aspect, the sheath interlock member is assembled to the tongue embracing member by an overmolding process.

In yet another aspect, the sheath interlock member is assembled to the tongue embracing member by slideably inserting a sheath interlock member base of the sheath interlock member into a receiving channel formed in the exterior surface of the dorsal side of the tongue embracing member.

In yet another aspect, the receiving channel formed in the exterior surface of the dorsal side of the tongue embracing member includes a first channel segment and a second channel segment located opposite the first channel segment.

In yet another aspect, the receiving channel formed in the exterior surface of the dorsal side of the tongue embracing member includes a first channel segment and a second channel segment located opposite the first channel segment, wherein the first channel segment and the second channel segment are generally perpendicular to a longitudinal axis of the tongue embracing member.

In yet another aspect, the receiving channel formed in the exterior surface of the dorsal side of the tongue embracing member includes a first channel segment and a second channel segment located opposite the first channel segment, wherein the first channel segment and the second channel segment are parallel to one another.

In yet another aspect, the receiving channel formed in the exterior surface of the dorsal side of the tongue embracing member further comprises a third channel segment, wherein the third channel segment spans between like ends of the first channel segment and the second channel segment, wherein the first channel segment, the third channel segment and the second channel segment collectively form a "U" shaped channel.

In yet another aspect, the receiving channel is spaced from the exterior surface of the dorsal side of the tongue embracing member by a channel riser feature, wherein the channel riser feature reduces transfer of torsional and/or sheer forces from the sheath interlock member to the tongue embracing member. The reduction in transfer of forces reduces a potential scenario which can separate an interior surface of the tongue embracing member from the user's tongue, which can result in separation and dislodgement of the tongue embracing member from the user's tongue, resulting in an ineffective device.

In yet another aspect, the sheath interlock member arm and the maxilla lip retention subassembly arm are assembled positioning mating surfaces contacting or against one another.

In yet another aspect, at least one of the sheath interlock member arm and the maxilla lip retention subassembly arm is formed having a changing thickness defining a tapering distal or outer surface.

In yet another aspect, the changing thickness of the at least one of the sheath interlock member arm and the maxilla lip retention subassembly arm is linear along at least a portion of a length of the respective at least one arm.

In yet another aspect, the changing thickness of the at least one of the sheath interlock member arm and the maxilla lip retention subassembly arm forms a curved or arched surface along at least a portion of a length of the respective at least one arm.

In yet another aspect, a position retaining member at least partially circumscribes an external periphery defined by an assembly of the sheath interlock member arm and the maxilla lip retention subassembly arm. The position retaining member can be formed having a tubular rectangle shape, a tubular oblong shape, an elliptical shape, and the like, wherein the preferred shape would mimic the cross sectional shape of the assembly of the sheath interlock member arm and the maxilla lip retention subassembly arm. An interior distance spanning between an interior transverse or upper surface and an interior opposite transverse or lower surface of the position retaining member is sized enabling a sliding motion between the sheath interlock member arm and the maxilla lip retention subassembly arm when positioned at a location of the assembly having a narrow thickness and restraining any sliding motion between the sheath interlock member arm and the maxilla lip retention subassembly arm when positioned at a location of the assembly having a wider thickness.

In yet another aspect, the mating surfaces of the sheath interlock member arm and the maxilla lip retention subassembly arm are smooth.

In yet another aspect, the mating surfaces of the sheath interlock member arm and the maxilla lip retention subassembly arm are textured to increase a frictional force generated therebetween.

In yet another aspect, the mating surfaces of the sheath interlock member arm and the maxilla lip retention subassembly arm are co-planar.

In yet another aspect, the mating surfaces of the sheath interlock member arm and the maxilla lip retention subassembly arm include a series of mating mechanically engaging features.

In yet another aspect, the mating surfaces of the sheath interlock member arm and the maxilla lip retention subassembly arm include a series of mating mechanically engaging features, wherein (a) in a condition where the series of mating mechanically engaging features are engaged with one another, the sheath interlock member arm and the maxilla lip retention subassembly arm are restrained from a sliding motion therebetween and (b) in a condition where the series of mating mechanically engaging features are disengaged or separated from one another, the sheath interlock member arm and the maxilla lip retention subassembly arm are capable of a sliding or linear repositioning motion between one another.

In yet another aspect, a position retaining member can be positioned against external surfaces of the sheath interlock member arm and the maxilla lip retention subassembly arm at a position having a thickness that is approximately equal to an distance between opposite, internal transverse surfaces of the position retaining member to retain engagement between mating mechanically engaging features, thus retaining an axial relationship between the sheath interlock member arm and the maxilla lip retention subassembly arm.

In yet another aspect, the mating surfaces of the sheath interlock member arm and the maxilla lip retention subassembly arm include a series of mating mechanically engaging features comprising a series of peaks and valleys.

In yet another aspect, the mating surfaces of the sheath interlock member arm and the maxilla lip retention subassembly arm include a series of mating mechanically engaging features comprising a series of peaks and valleys, wherein the peaks and valleys are linear and spatially arranged.

In yet another aspect, the mating surfaces of the sheath interlock member arm and the maxilla lip retention subassembly arm include a series of mating mechanically engaging features comprising a series of peaks and valleys, wherein are linear, oriented substantially parallel to one another, and spatially arranged.

In yet another aspect, the mating surfaces of the sheath interlock member arm and the maxilla lip retention subassembly arm include a series of mating mechanically engaging features comprising a series of peaks and valleys, wherein the peaks and valleys are linear, oriented substantially perpendicular to a longitudinal axis of each arm, and spatially arranged.

In yet another aspect, the mating surfaces of the sheath interlock member arm and the maxilla lip retention subassembly arm include a series of mating mechanically engaging features comprising a series of peaks and valleys, wherein the peaks and valleys are linear and equally spaced arranged.

In yet another aspect, at least one of the sheath interlock member arm and the maxilla lip retention subassembly arm further comprises a position retaining member retention feature.

In yet another aspect, at least one of the sheath interlock member arm and the maxilla lip retention subassembly arm further comprises a position retaining member retention feature, wherein the position retaining member retention feature is a boss or other outwardly extending feature located proximate a distal end of the associated arm.

In yet another aspect, the maxilla lip retention subassembly comprises a lip retention feature. The lip retention feature can formed in any suitable shape for comfortably retaining the patient's maxilla lip.

In yet another aspect, the lip retention feature is fabricated inclusive of a pliant material. The pliant material may be silicone, nylon, rubber, plastic, wax, and the like.

In yet another aspect, the lip retention feature can be shaped to engage with a gum line of the patient.

In yet another aspect, the tongue embracing member comprises an air extraction valve.

In yet another aspect, the air extraction valve includes a valve seal that opens outward from a sealing feature.

In yet another aspect, the sealing feature is a flange circumscribing an interior circumference of an air extraction tube comprising the air extraction valve.

In yet another aspect, the air extraction valve includes a valve seal that pivotally opens outward from the sealing feature.

In yet another aspect, the valve seal is in operational communication with a valve operational handle.

In yet another aspect, the valve operational handle is operated by a mechanical interference with a feature and/or surface of a bulb air extraction tube of an air extraction device.

In yet another aspect, the valve operational handle includes at least one of a magnet and a magnetically attracting material and the bulb air extraction tube of an air extraction device comprises a mating at least one of a magnet and a magnetically attracting material, thus resulting in a magnetic attraction between the two elements. The magnetic attraction draws the valve seal into a closed or sealed configuration when the bulb air extraction tube of the air extraction device is slideably removed from the tongue embracing member air extraction tube.

In yet another aspect, at least one of the valve operational handle and the valve seal is in operational communication with a biasing element. The biasing element can be any form of a biasing element, including a coil spring, a cantilever spring, and the like.

In yet another aspect, the bulb air extraction tube further comprises a lead in feature, wherein one exemplary lead in feature is chamfered interior surface.

In yet another aspect, the bulb air extraction tube further comprises a valve insertion stop seat, wherein the valve insertion stop seat limits the sliding motion between the tongue embracing member air extraction tube and the interior surface of the bulb air extraction tube of the air extraction device.

In yet another aspect, the valve insertion stop seat is formed as an internal ridge at least partially circumscribing the interior surface of the bulb air extraction tube of the air extraction device.

In yet another aspect, the tongue embracing member air extraction tube includes an air extraction valve clearance, providing a clearance for the valve flap when the valve flap is rotated into an open configuration.

In yet another aspect, a vacuum formed within the tongue embracing member retains the valve flap in a closed configuration.

In yet another aspect, a sheath tongue sealing ridge is formed along at least a portion of a contacting circumferential surface of an interior surface of the tongue embracing member.

These and other advantages of the invention will be further understood and appreciated by those skilled in the art by reference to the following written specification, claims and appended drawings.

BRIEF DESCRIPTION OF THE DRAWINGS

The invention will now be described, by way of example, with reference to the accompanying drawings, in which:

FIG. 15 presents an isometric view of a dorsal side of a second exemplary tongue attachment member, the second exemplary tongue attachment member provides an attachment interface for any oral supporting device, including sleep apnea, a lip retention member, and the like;

FIG. 22 presents an isometric view of a dorsal side of a third exemplary tongue attachment member, the third exemplary tongue attachment member provides an attachment interface for any oral supporting device, including sleep apnea, a lip retention member, and the like;

FIG. 34 presents an isometric, partially exploded assembly view of a dorsal side of a fifth exemplary tongue attachment member, wherein the fifth exemplary tongue attachment member is a variant of the third and fourth exemplary tongue attachment members introduced in FIGS. 22 and 29 respectively, wherein a sheath interlock member is slideably assembled to a channel formed in the dorsal side of the tongue attachment member body;

FIG. 35 presents a sectioned view of the fifth tongue attachment member taken along section 35-35 of FIG. 34, wherein the illustration presents a bulb air extraction tube of an air extraction device prior to insertion onto an air extraction valve;

FIG. 36 presents a sectioned view of the fifth tongue attachment member taken along section 35-35 of FIG. 34, wherein the illustration presents the bulb air extraction tube of the air extraction device following insertion onto the air extraction valve;

Like reference numerals refer to like parts throughout the various views of the drawings.

DETAILED DESCRIPTION OF THE INVENTION

Figure 1:
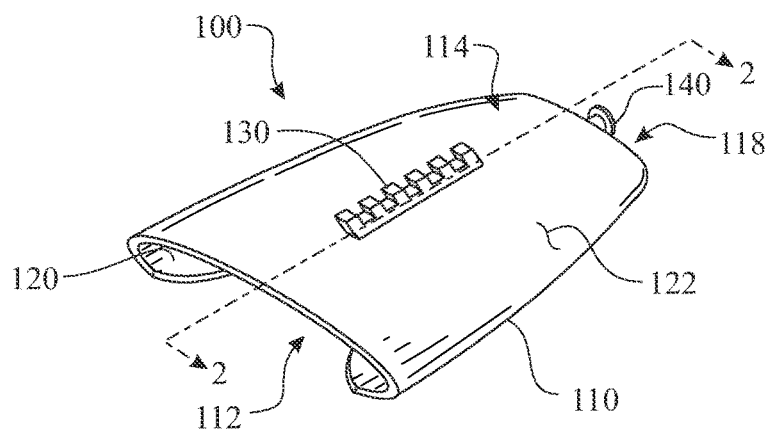
FIG. 1 presents an isometric view of a dorsal side of a first exemplary tongue attachment member of a sleep apnea control device.
Figure 2:
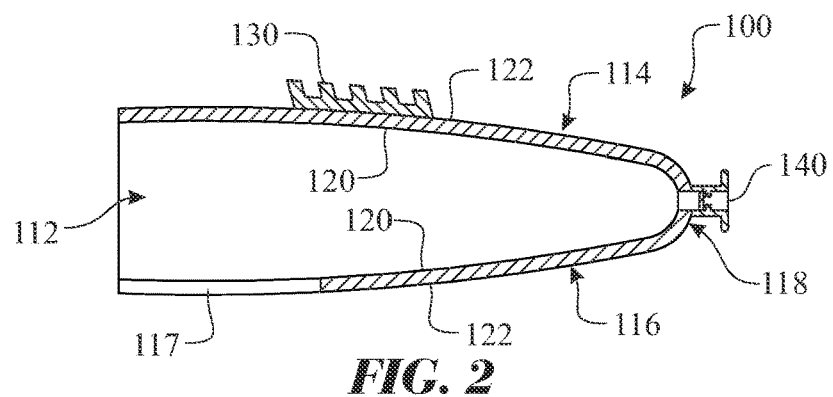
FIG. 2 presents a sectioned view of the tongue attachment member introduced in FIG. 1, the section being taken along section 2-2 of FIG. 1.
Figure 3:
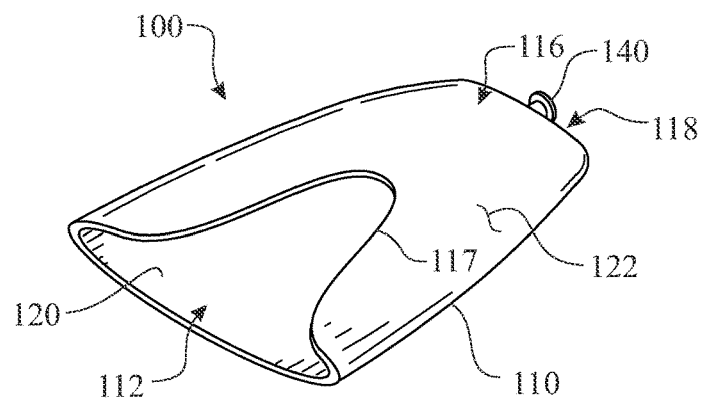
FIG. 3 presents an isometric view of a ventral side of the tongue attachment member.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

A sleep apnea control device is provided for the prevention of snoring and sleep apnea. The sleep apnea control device includes a tongue attachment subassembly 100 and a maxilla attachment subassembly 200, as illustrated in FIG. 11.

Figure 10:
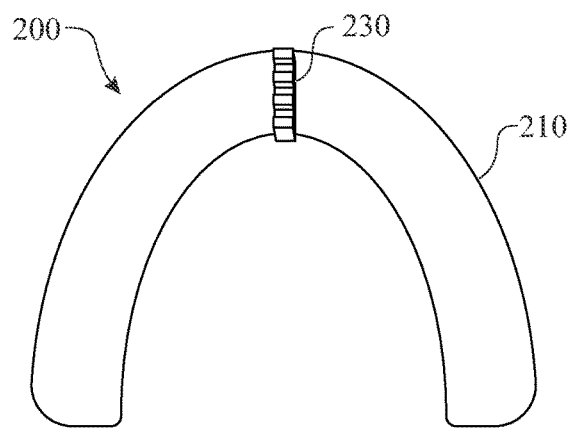
FIG. 10 presents a bottom side plan view of a maxilla attachment member of the apnea control device.

The tongue attachment subassembly 100 is detailed in FIGS. 1 through 9. The maxilla attachment subassembly 200 is detailed in FIG. 10. The tongue attachment subassembly 100 includes a sheath 110, wherein the sheath 110 is defined having a tongue receiving cavity 112 for insertion of an individual's tongue 300. The tongue attachment subassembly 100 can be defined having a dorsal side 114 and a ventral side 116. The sheath 110 can also be defined having an exterior surface 120 and a tongue engagement surface 122. An air extraction valve 140 is integrated into the sheath 110 at a sheath distal end 118. The illustrated air extraction valve 140 is only exemplary and it is understood that it can include any unidirectional valve known by those skilled in the art. The device may be fabricated from any of a plethora of known, non-toxic materials. The sheath 110 is fabricated of a pliant material, such as latex, silicone, rubber, and the like. The sheath 110 can be molded, thermally formed, or constructed using similarly known fabrication techniques.

Figure 7:
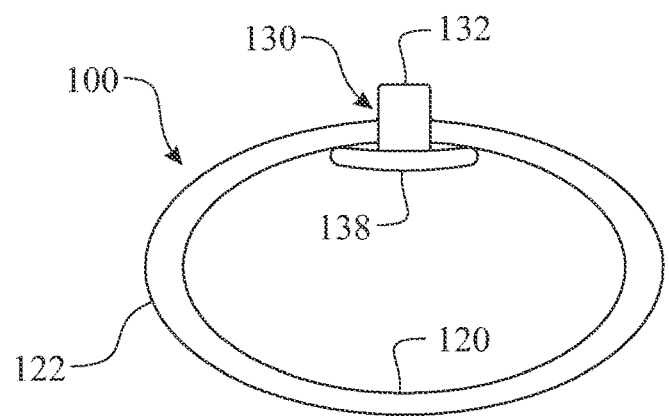
FIG. 7 presents an anterior elevation view of the tongue attachment member.

A sheath interlock member 130 is integrated into a dorsal side 114 portion of the sheath 110. Details of the sheath interlock member 130 are presented in FIG. 6. The sheath interlock member 130 includes an interlock ridge 132 having a series of interlock teeth 134 and interlock teeth-receiving receptacle 136 extending outward from the tongue engagement surface 122 of the dorsal side 114. The preferred design orients the interlock teeth 134 and interlock teeth-receiving receptacle 136 such that a base of each interlock teeth 134 is slightly forward of its top of the respective interlock teeth 134. The sheath interlock member 130 can be integrated into the sheath 110 during the fabrication of the tongue attachment subassembly 100 using the same material, using a different material, or joined in a post fabrication assembly step. The sheath interlock member 130 can include an optional interlock base portion 138 for attachment to the sheath 110. The interlock base portion 138 can be formed having an arched shape with a downward apex, wherein the apex applies additional pressure to the individual's tongue 300. The interlock ridge 132 is inserted through an aperture formed in the dorsal side 114 and attached using any adequate attachment means. An exemplary attachment bonds the interlock base portion 138 to the exterior surface 120 using a bonding media, as illustrated in FIG. 7. The sheath interlock member 130 is preferably constructed from a rigid material, such as plastic, hard rubber, nylon, and the like. The sheath interlock member 130 is preferably fabricated using a molding process, but it is recognized that the sheath interlock member 130 can be fabricated using any reasonable process respective to the material selection. The bonding can be provided using any bonding medium, using a heat staking process, using an ultrasonic welding process, and the like.

Figure 4:
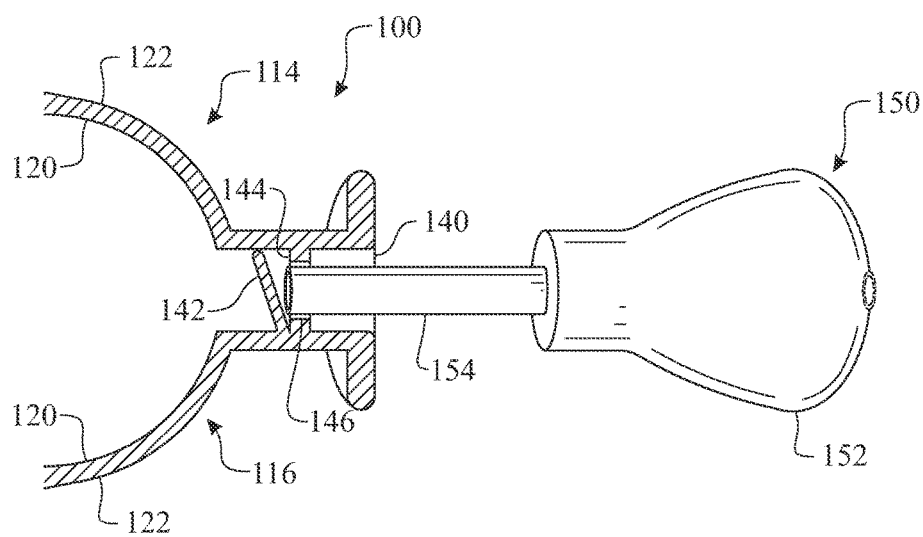
FIG. 4 presents an enlarged sectioned view of a distal end of the tongue attachment member, detailing an air removal system.
Figure 5:
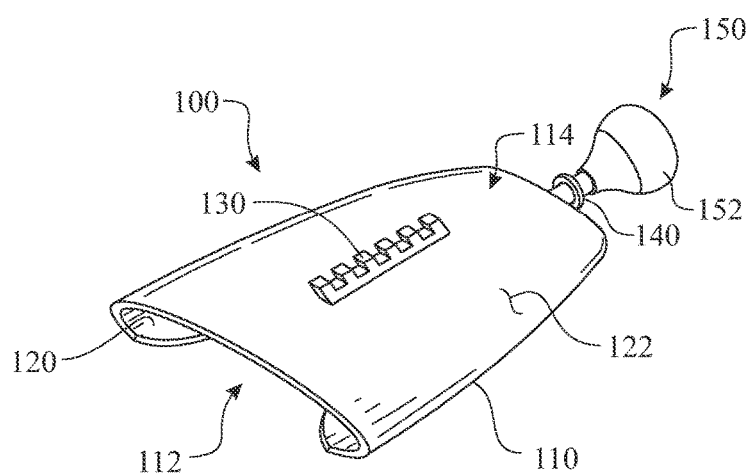
FIG. 5 presents an isometric view of the dorsal side of the tongue attachment member and the air removal system.
Figure 6:
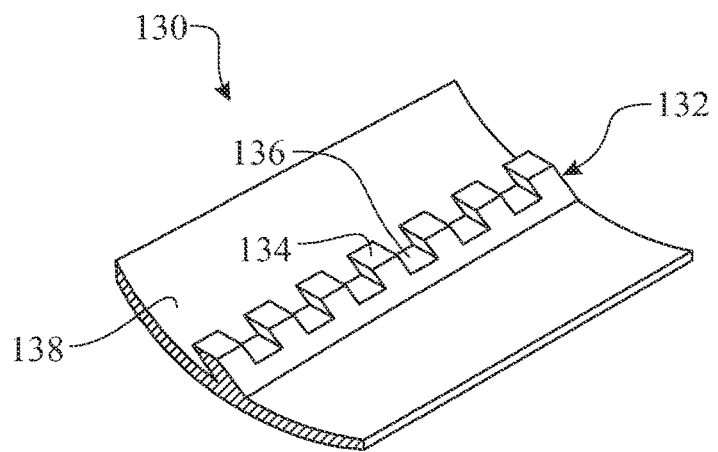
FIG. 6 presents an isometric view of a sheath interlock member.
Figure 8:
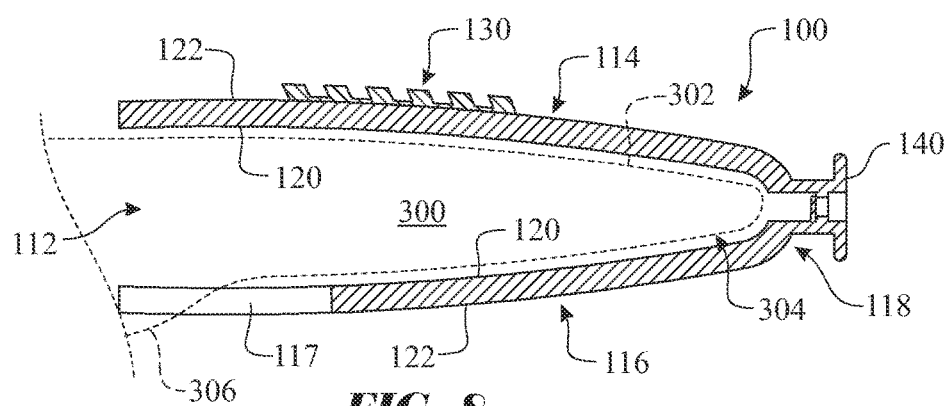
FIG. 8 presents a side sectioned view of the tongue attachment member taken along a longitudinal centerline, wherein the tongue attachment member is secured to an individual's tongue.
Figure 9:
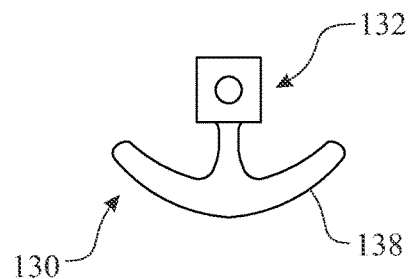
FIG. 9 presents an end elevation view of the sheath interlock member.
Figure 11:
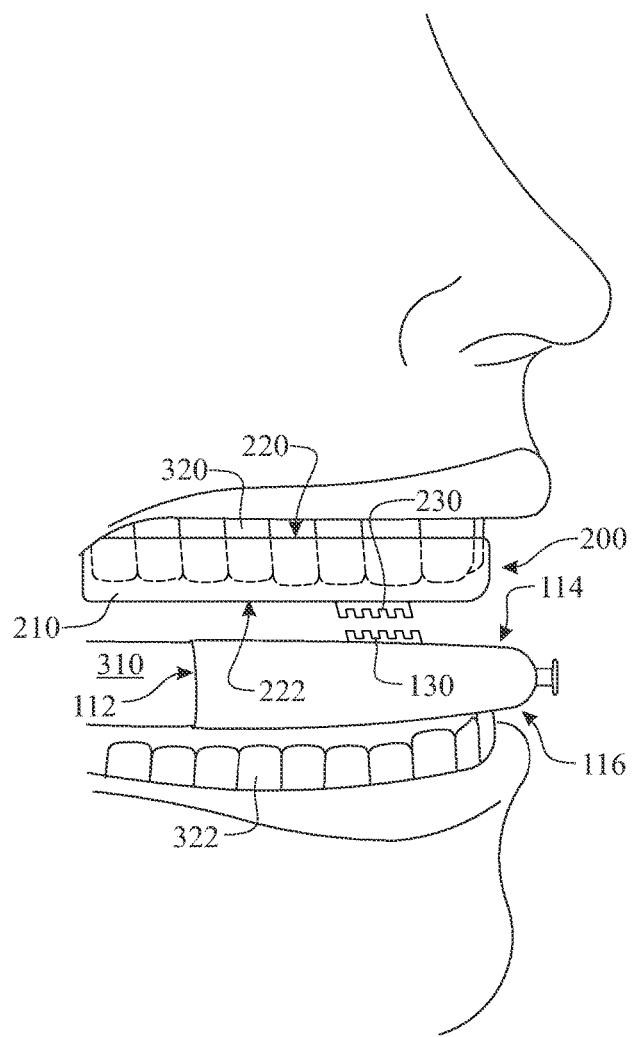
FIG. 11 presents a side elevation view of the apnea control device demonstrating proper positioning within an individual's mouth.

The tongue attachment subassembly 100 is placed over and secured to an individual's tongue 300 as illustrated in a FIGS. 8 and 11. A tongue base clearance 117 can be formed within the ventral side 116 of the sheath 110, providing a clearance for a tongue base 306. The tongue base clearance 117 is a recess in the ventral side 116 of the sheath 110, extending inward from an opening for the tongue receiving cavity 112. A securing seal is created by evacuating air from a gap 304 formed between a tongue surface 302 of the individual's tongue 300 and the tongue engagement surface 122. As the sheath 110 is placed upon the individual's tongue 300, air within the tongue receiving cavity 112 is displaced and a seal is created between the tongue surface 302 and a rear portion of sheath 110. A majority of the remaining air is removed using an air removal system. The air removal system includes an air extraction valve 140 and an air extraction device 150. The air extraction device 150 engages with the air extraction valve 140 to extract air from the gap 304. Details of the air removal system are illustrated in FIG. 4. The air extraction device 150 includes an air extraction bulb 152 in fluid communication with an air extraction pipette 154. In the exemplary embodiment, the air extraction pipette 154 is inserted through a unidirectional valve orifice 146 separating a unidirectional valve flap 142 from a unidirectional valve seal 144. This creates an airflow passage between the gap 304 and the air extraction bulb 152. The user would preferably squeeze the air extraction bulb 152 to discharge air from within the air extraction bulb 152 prior to insertion of the air extraction pipette 154 through the unidirectional valve orifice 146. Once inserted, the user would release the pressure from the air extraction bulb 152, thus causing the air extraction bulb 152 to extract air from the gap 304. The user then removes the air extraction device 150 from the air extraction valve 140. The unidirectional valve flap 142 naturally retracts to a sealed configuration, seating against the unidirectional valve seal 144. The removal of air from the gap 304 creates a vacuum, which secures the sheath 110 onto the individual's tongue 300. It is understood that although the illustrations present a removable air extraction device 150, the air extraction device 150 can alternately be integrated into the air extraction valve 140. The air extraction device 150 can be used to aid in the return of air into the air-extracted region to aid in removal of the tongue attachment subassembly 100 from the individual's tongue 300.

The maxilla attachment subassembly 200 is formed of a resilient material and shaped to be removably attached to a maxilla (upper jaw) 320. The maxilla attachment subassembly 200 includes a maxilla tray 210, which is formed in a "U-shape", contouring to the maxilla (upper jaw) 320. The maxilla tray 210 is defined having a maxilla tray's attachment side 220 and a maxilla tray's interlock side 222. The maxilla tray's interlock side 222 includes a recession formed into the maxilla tray 210 for receiving individual's teeth. The maxilla attachment subassembly 200 is fabricated having a tray interlock member 230 disposed upon the maxilla tray's interlock side 222 of the maxilla tray 210. The maxilla tray 210 is shaped to be removably attached to the maxilla (upper jaw) 320.

Figure 12:
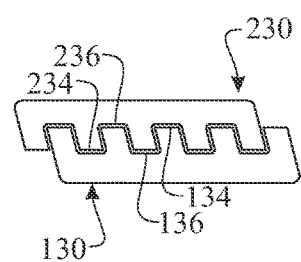
FIG. 12 presents a side elevation view of the tray interlock member engaged with the sheath interlock member.

The maxilla tray 210 is secured by its shape and can optionally include one or more features to aid in the engagement with the individual's teeth. The maxilla tray 210 can be formed to mate with the maxilla (upper jaw) 320 by placing the maxilla attachment subassembly 200 into hot water, inserting the maxilla attachment subassembly 200 into the individual's mouth, and placing with finger pressure into an interior recession. This will shape the interior portion of the maxilla tray 210 to mate with the maxilla (upper jaw) 320. Another technique to form the maxilla tray 210 is to have a custom maxilla tray 210 fabricated by the individual's dentist or other oral health care professional. This technique allows the maxilla tray 210 to be custom fit for the user. The custom version of the maxilla attachment subassembly 200 would be fabricated in a manner similar to that for teeth whitening trays from their dentist. A tray interlock member 230 is positioned onto the maxilla tray 210 to interlock with the sheath interlock member 130 as illustrated in FIGS. 11 and 12. An interlock is formed by an engagement between the interlock teeth 134 of the sheath interlock member 130 and the interlock tooth receptacle 236 of the tray interlock member 230, and similarly with the engagement between the interlock tooth 234 of the tray interlock member 230 and the interlock teeth-receiving receptacle 136 of the sheath interlock member 130. The interlock between the sheath interlock member 130 and the tray interlock member 230 draws and maintains the individual's tongue 300 forward, to an extended tongue 310. The teeth engage by the angled relation of the between the interlock tooth 234 and the interlock teeth-receiving receptacle 136. The extended tongue 310 is positioned, resting upon teeth and/or gums of an individual's mandible (lower jaw) 322. The extended tongue 310 and the fixed position of the jaw will reduce or eliminate snoring and sleep apnea.

The sleep apnea control device can be removed from the individual's mouth by opening the individual's mouth, which separates the engaged sheath interlock member 130 and tray interlock member 230, removing the maxilla attachment subassembly 200, then releasing the vacuum holding the tongue attachment subassembly 100 and removing the tongue attachment subassembly 100 from the individual's tongue 300. The vacuum can be removed by squeezing the two sides of the tongue attachment subassembly 100 together to separate the rear edge from the individual's tongue 300 or by inserting the air extraction pipette 154 into the air extraction valve 140, which separates the unidirectional valve flap 142 from the unidirectional valve seal 144, and squeezing the air extraction bulb 152 to inject air into the tongue receiving cavity 112. Upon combining the fixed, forward location 310 of a user's tongue 300 with adequate, uniform suction between the user's tongue 300 and the sheath 310, a comfortable and efficient oral medical apparatus used in the prevention of snoring and sleep apnea is realized.

Although the exemplary embodiments include the air extraction valve 140, it is understood that the tongue attachment subassembly 100 can be fabricated excluding the air extraction valve 140. The user would manually remove the air within the tongue surface 302 by sucking the air therefrom.

Figure 13:
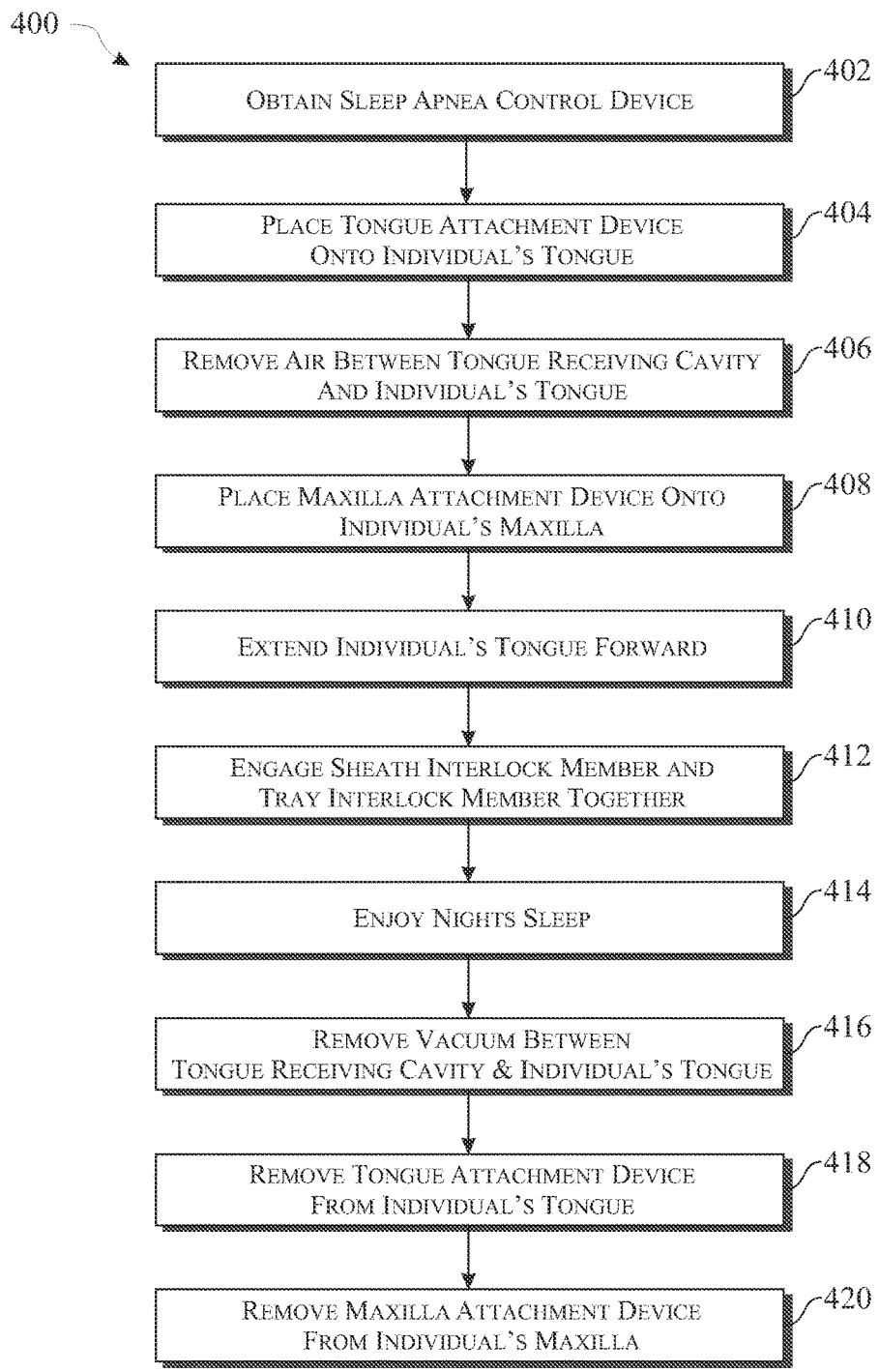
FIG. 13 presents an exemplary flow diagram illustrating a method of use of the sleep apnea control device.

An exemplary sleep apnea control method flow diagram 400 is presented in FIG. 13. The method initiates with a step of the individual obtaining the sleep apnea control device (step 402), the device comprising the tongue attachment member 100 and the maxilla attachment subassembly 200. The user places their tongue 300 into the tongue receiving cavity 112 in accordance with a tongue attachment subassembly installation step (step 404). The user removes a majority of the residual air remaining between the tongue engagement surface 122 of the tongue receiving cavity 112 and the individual's tongue 300 in accordance with an air removal step (step 406). The maxilla attachment subassembly 200 is positioned, placing the maxilla tray's attachment side 220 against the individual's maxilla (upper jaw) 320 in accordance with a maxilla attachment subassembly installation step (step 408). The process continues with the user extending their tongue 300 (tongue extending step 410) and engaging the sheath interlock member 130 and the tray interlock member 230 together, referred to as an interlock engagement step (step 412). At this point, the device is ready for use and the individual can enjoy a night's sleep (step 414). Upon completion of use, the individual disengages the interlock provided between the sheath interlock member 130 and the tray interlock member 230. The user opens their mouth and removes the vacuum provided between the tongue receiving cavity 112 and the individual's tongue 300 in accordance with a vacuum removal step (step 416). Once released, the user removes the tongue attachment subassembly 100 from their tongue 300 per a tongue attachment subassembly removal step (step 418). The use is concluded with the removal of the maxilla attachment subassembly 200 from the individual's maxilla (upper jaw) 320 in accordance with a maxilla attachment subassembly removal step (step 420). The user then stores the sleep apnea control device for future use.

Figure 14:
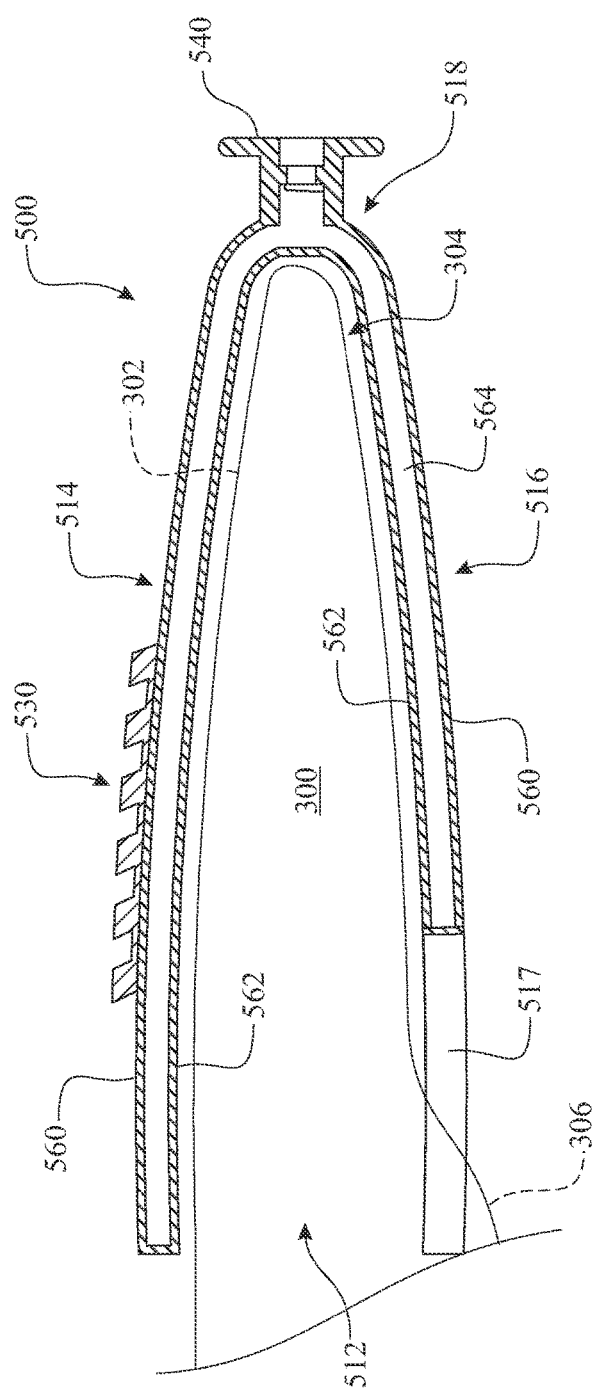
FIG. 14 presents a side sectioned view of an alternate tongue attachment member taken along a longitudinal centerline, wherein the tongue attachment member is secured to an individual's tongue.
Figure 15:
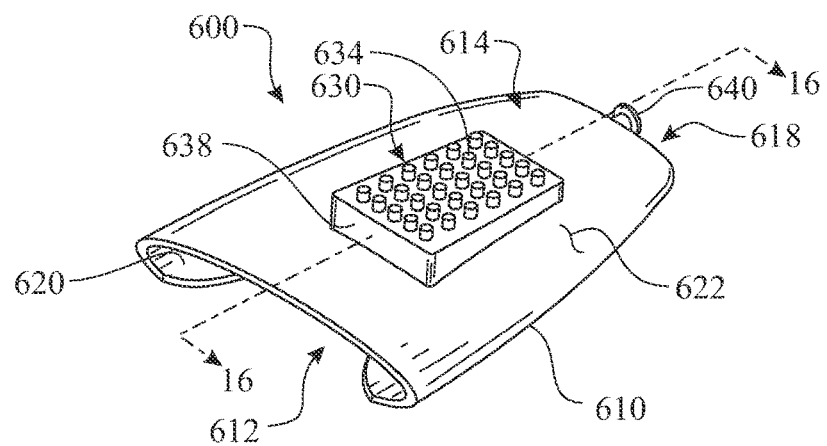
Figure 16:
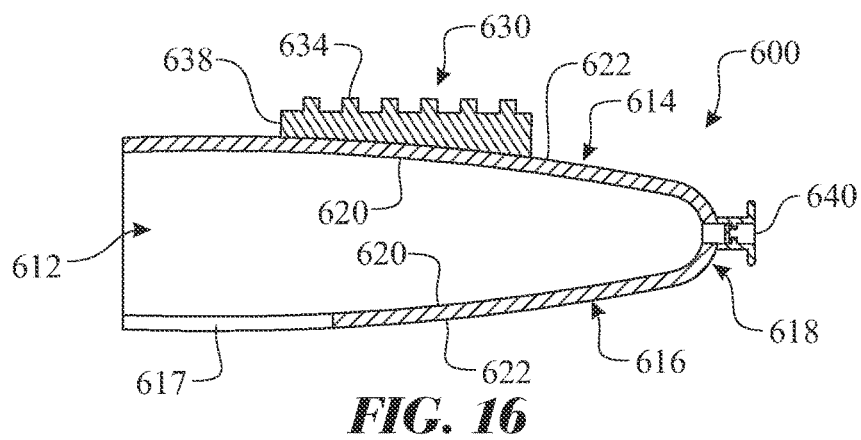
FIG. 16 presents a sectioned view of the second tongue attachment member taken along section 16-16 of FIG. 15.
Figure 17:
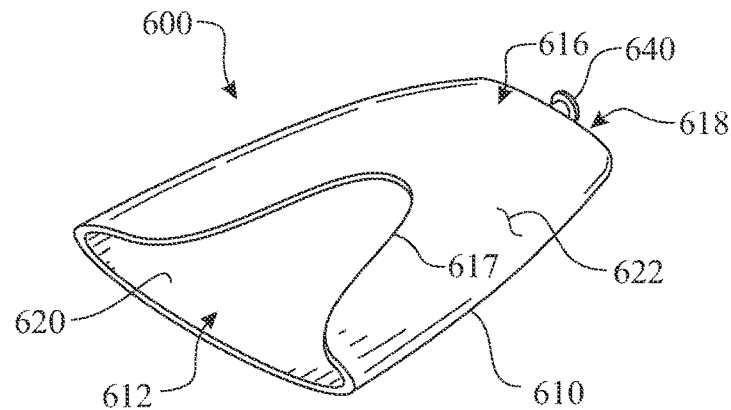
FIG. 17 presents an isometric view of a ventral side of the second tongue attachment member.
Figure 18:
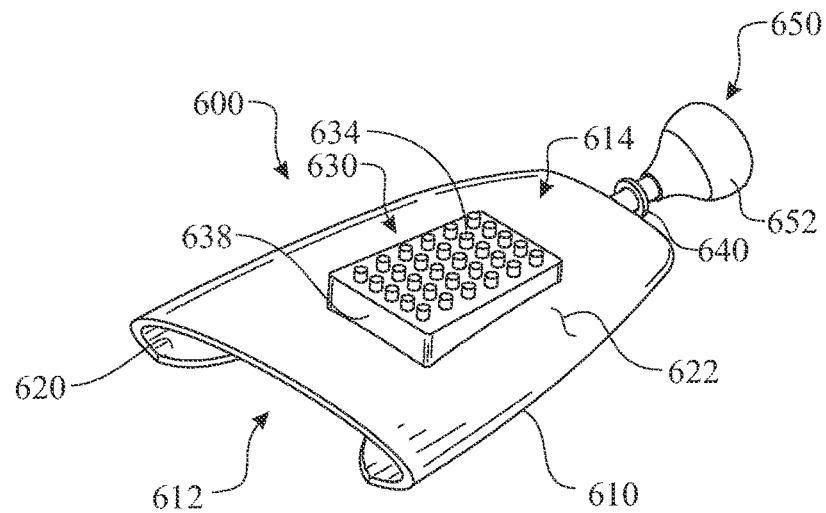
FIG. 18 presents an isometric view of the dorsal side of the second tongue attachment member and the air removal system.

An alternate embodiment of the tongue embracing member 100 is presented as a tongue embracing member 500 illustrated in FIG. 14. Like features of tongue embracing member 500 and tongue embracing member 100 are numbered the same except preceded by the numeral '5'. The tongue embracing member 500 utilizes an internally provided suction compared to the tongue embracing member 100, which utilizes an externally applied suction. The tongue embracing member 500 is fabricated having a bladder air chamber 564 formed therein. The bladder air chamber 564 is defined by a bladder interior wall 562 formed on the tongue-contacting portion of the tongue embracing member 500 and a bladder exterior wall 560 formed on the external portion of the tongue embracing member 500. The user would remove the air from within the bladder air chamber 564 drawing and securing the tongue embracing member 500 onto the individual's tongue 300. The tongue embracing member 500 would be shaped to include a tongue base clearance 117.

The tongue embracing member 100 can be adapted to include an array arrangement of interlocking pins 634, wherein the adapted assembly is referred to as a tongue embracing member 600 and is illustrated in FIGS. 15 through 18. Like features of tongue embracing member 600 and tongue embracing member 100 are numbered the same except preceded by the numeral '6'. Although the tongue embracing member 600 is illustrated formed having a solid material, it is understood that the tongue embracing member 600 can be formed having a bladder similar to the tongue embracing member 500.

Figure 19:
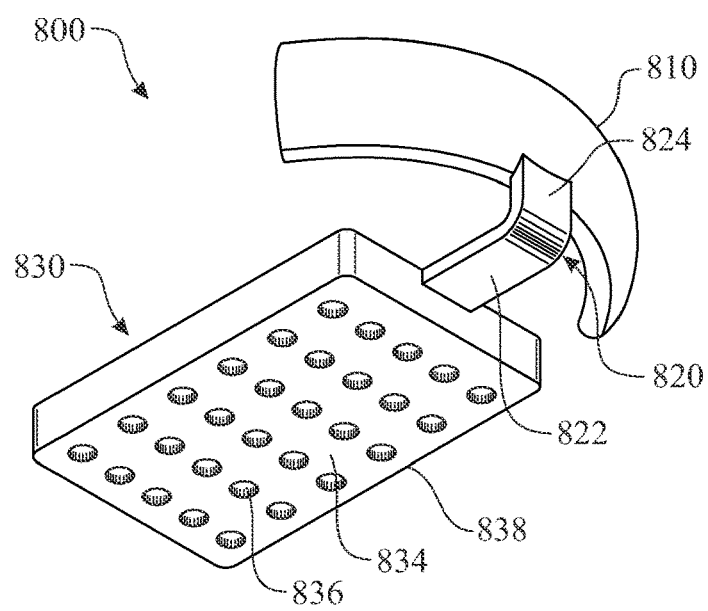
FIG. 19 presents an isometric view of an exemplary maxilla lip retention subassembly for use in conjunction with the second tongue attachment member.

The array arrangement of interlocking pins 634 extends perpendicularly from an interlock base portion 638. The array arrangement of interlocking pins 634 provides longitudinal and axial adjustments between the tongue embracing member 600 and another component. One exemplary component for use in conjunction with the tongue embracing member 600 would be a maxilla lip retention subassembly 800, which is introduced in FIG. 19. The maxilla lip retention subassembly 800 includes a lip retention subassembly interlock member 830 distally attached to a lip retention section 810 by a maxilla lip retention positioning arm 820. The maxilla lip retention positioning arm 820 can be designed having any suitable shape to appropriately position the lip retention section 810 when the maxilla lip retention subassembly 800 is attached to the tongue embracing member 600. The exemplary maxilla lip retention positioning arm 820 is shaped to include a positioning arm lateral arm 822 extending forward from the interlock base portion 638 and a positioning arm riser arm 824 extending downward from the lip retention section 810. The lip retention subassembly interlock member 830 can be provided in any configuration to detachably mate with the selected design of the sheath interlock member 630.

Figure 21:
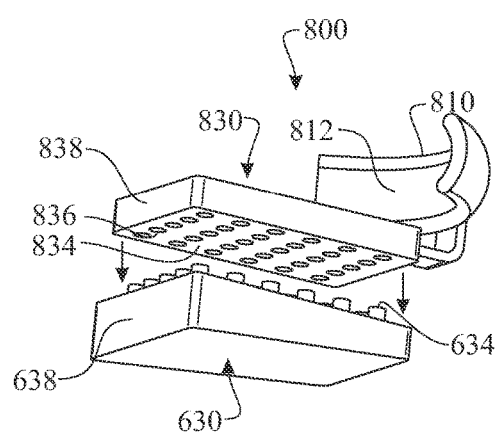
FIG. 21 presents an isometric view of the maxilla lip retention subassembly being attached to the tongue attachment member.
Figure 22:
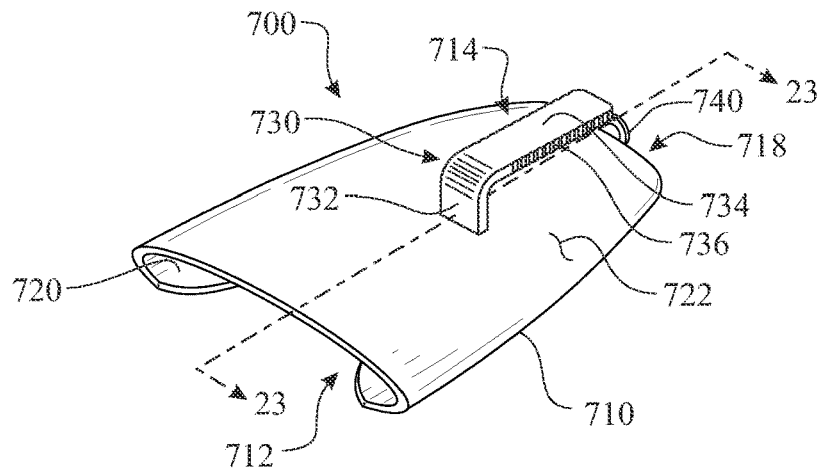
Figure 23:
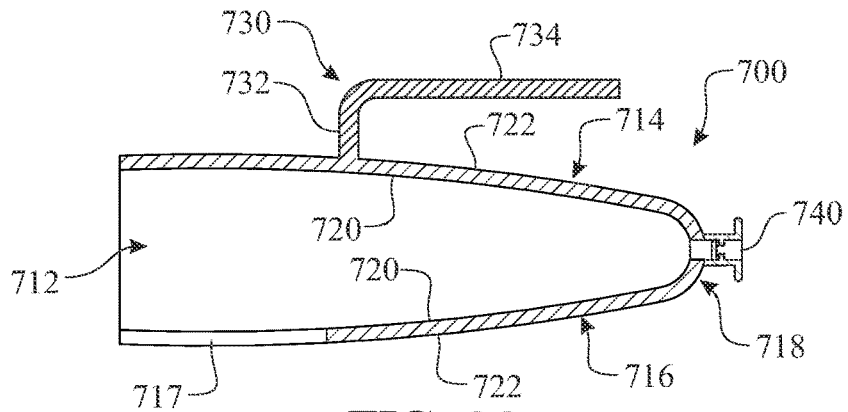
FIG. 23 presents a sectioned view of the third tongue attachment member taken along section 23-23 of FIG. 22.
Figure 24:
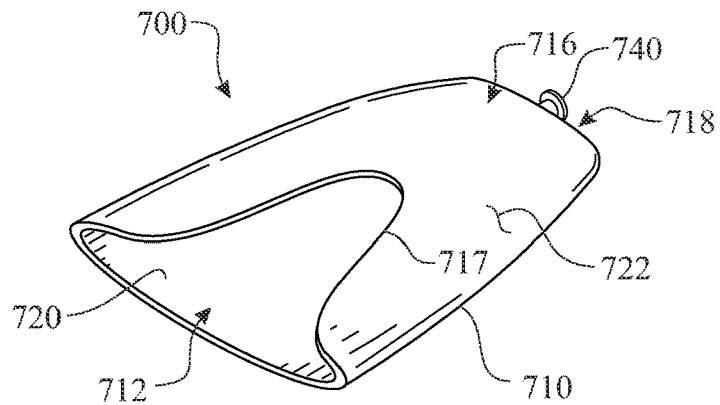
FIG. 24 presents an isometric view of a ventral side of the third tongue attachment member.
Figure 25:
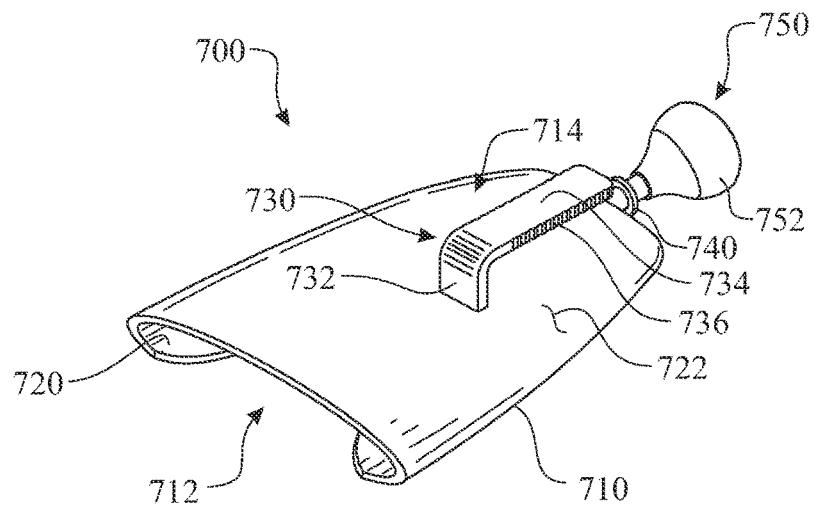
FIG. 25 presents an isometric view of the dorsal side of the third tongue attachment member and the air removal system.

The lip retention subassembly interlock member 830 includes an array of interlock pin receptacles 836 extending inward from an interlocking member contact surface 834 of an interlock base portion 838. The array of interlock pin receptacles 836 is arranged to detachably engage with the array of interlock pins 634. The array enables the user to positionally adjust the maxilla lip retention subassembly 800 in either or both a longitudinal and/or a lateral direction. The user would align the array of interlock pin receptacles 836 with the array of interlock pins 634 at the desired position and engage them accordingly as illustrated in FIG. 21.

Figure 20:
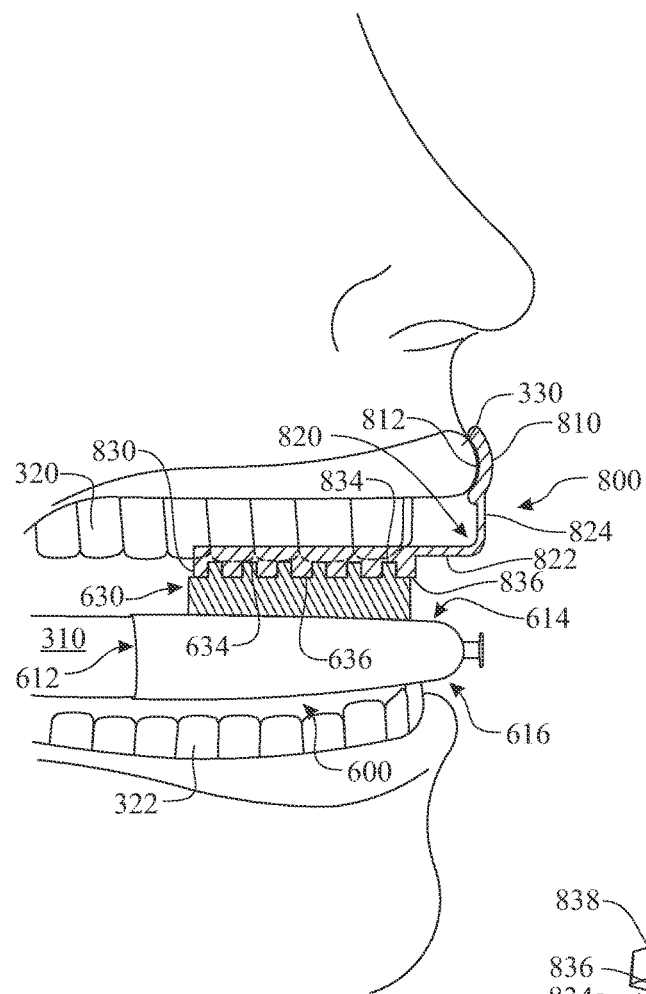
FIG. 20 presents a partially sectioned side view of the maxilla lip retention subassembly taken along a longitudinal centerline shown in use, wherein the maxilla lip retention subassembly is adapted to the secured tongue attachment member.

The exemplary maxilla lip retention subassembly 800 is shown in use in FIG. 20. The lip retention subassembly interlock member 830 of the maxilla lip retention subassembly 800 is engaged with the sheath interlock member 630 of the tongue embracing member 600. The user can positionally adjust the lip retention subassembly interlock member 830 respective to the sheath interlock member 630 to extend or retract the lip retention section 810. The tongue embracing member 600 would be secured to the tongue 310 of the patient as previously described. The lip retention subassembly interlock member 830 can be attached to the sheath interlock member 630 either prior to or subsequent to attachment of the tongue embracing member 600 to the tongue 310. The lip retention section 810 would retain an upper lip 330 of the patient in a desired position. The assembly between the maxilla lip retention subassembly 800 and the tongue embracing member 600 would additionally retain the tongue 310 in a desired position. The lip retention section 810 would be fabricated of a pliant material to ensure comfort during use. The pliant material can be silicone, rubber, nylon, wax, plastic, and the like. The lip retention section 810 would preferably be formed in a "C" shape. The lip retention surface 812 can be formed having an arch to improve the support of the upper lip 330.

Although the exemplary embodiment of the lip retention section 810 contacts the upper lip 330 of the individual, it is understood that the lip retention section 810 can be shaped to contact a gum line of the individual for applications where the goal is to govern a position of the tongue 310.

It is understood that the maxilla attachment device 200 can be adapted for use with the tongue embracing member 600 by replacing the tray interlock member 230 with the lip retention subassembly interlock member 830.

The tongue embracing member 100 can be adapted to include a sheath interlock member 730, wherein the adapted device is referred to as a tongue embracing member 700 and is illustrated in FIGS. 22 through 25. Like features of tongue embracing member 700 and tongue embracing member 100 are numbered the same except preceded by the numeral '7'. Although the tongue embracing member 700 is illustrated formed having a solid material, it is understood that the tongue embracing member 700 can be formed having a bladder similar to the tongue embracing member 500.

The tongue embracing member 700 provides a sheath interlock member 730 in a form of a cantilevered member that extends forward above an exterior surface 722 of a dorsal side 714 of a sheath 710. The sheath interlock member 730 includes an interlock member riser segment 732 preferably extending generally perpendicular from the exterior surface 722. The interlock member riser segment 732 transitions into an interlock member engagement segment 734, which is preferably oriented in a parallel arrangement with a longitudinal axis of the sheath 710. An interlock member positioning feature 736 comprises a series of notches along at least one of an edge, an upper surface, and a lower surface of the interlock member engagement segment 734. The interlock member positioning feature 736 is provided to engage with a mating feature to axially position a mating member.

Figure 26:
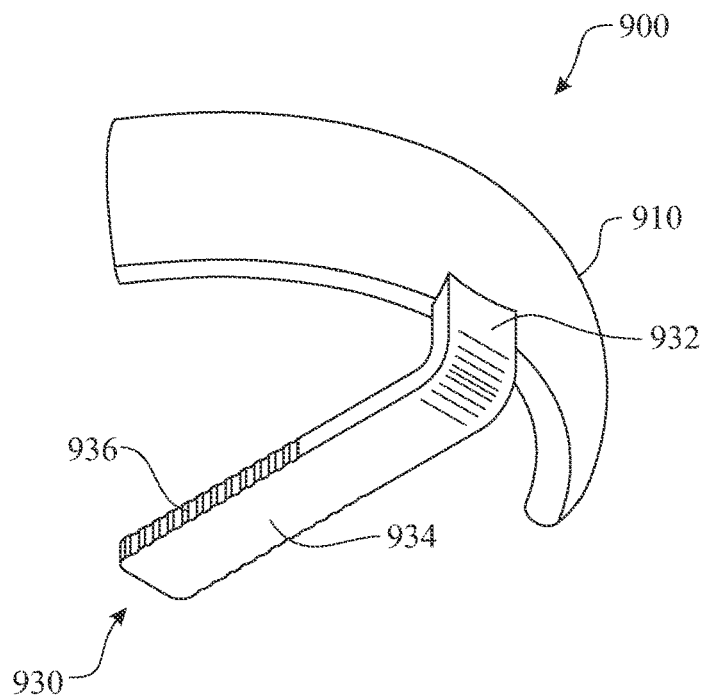
FIG. 26 presents an isometric view of an exemplary maxilla lip retention subassembly for use in conjunction with the third tongue attachment member.
Figure 28:
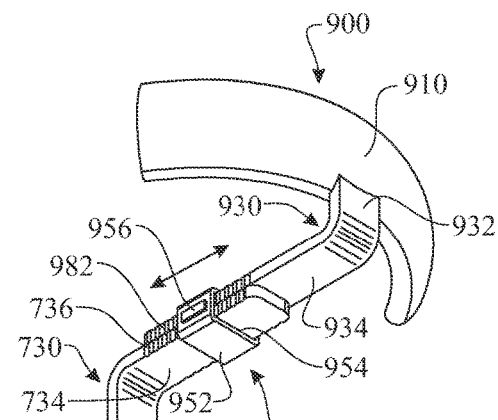
FIG. 28 presents an isometric view of the maxilla lip retention subassembly attached to the tongue attachment member in preparation for use.
Figure 27:
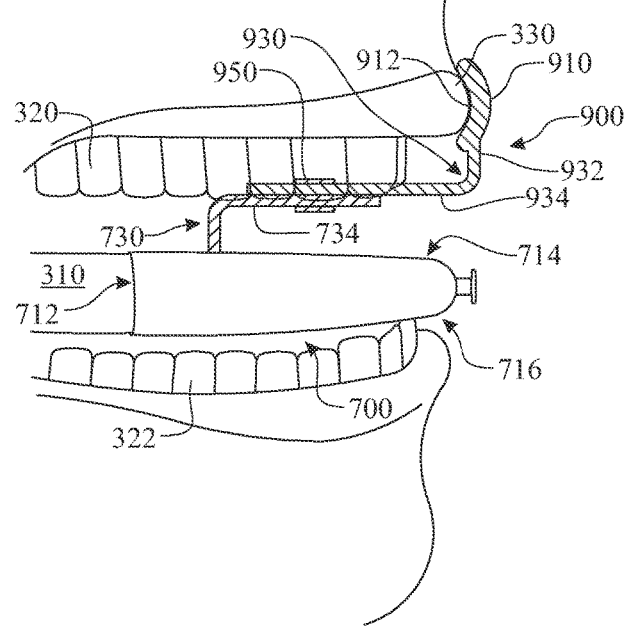
FIG. 27 presents a partially sectioned side view of the maxilla lip retention subassembly taken along a longitudinal centerline shown in use, wherein the maxilla lip retention subassembly is adapted to the secured tongue attachment member.
Figure 29:
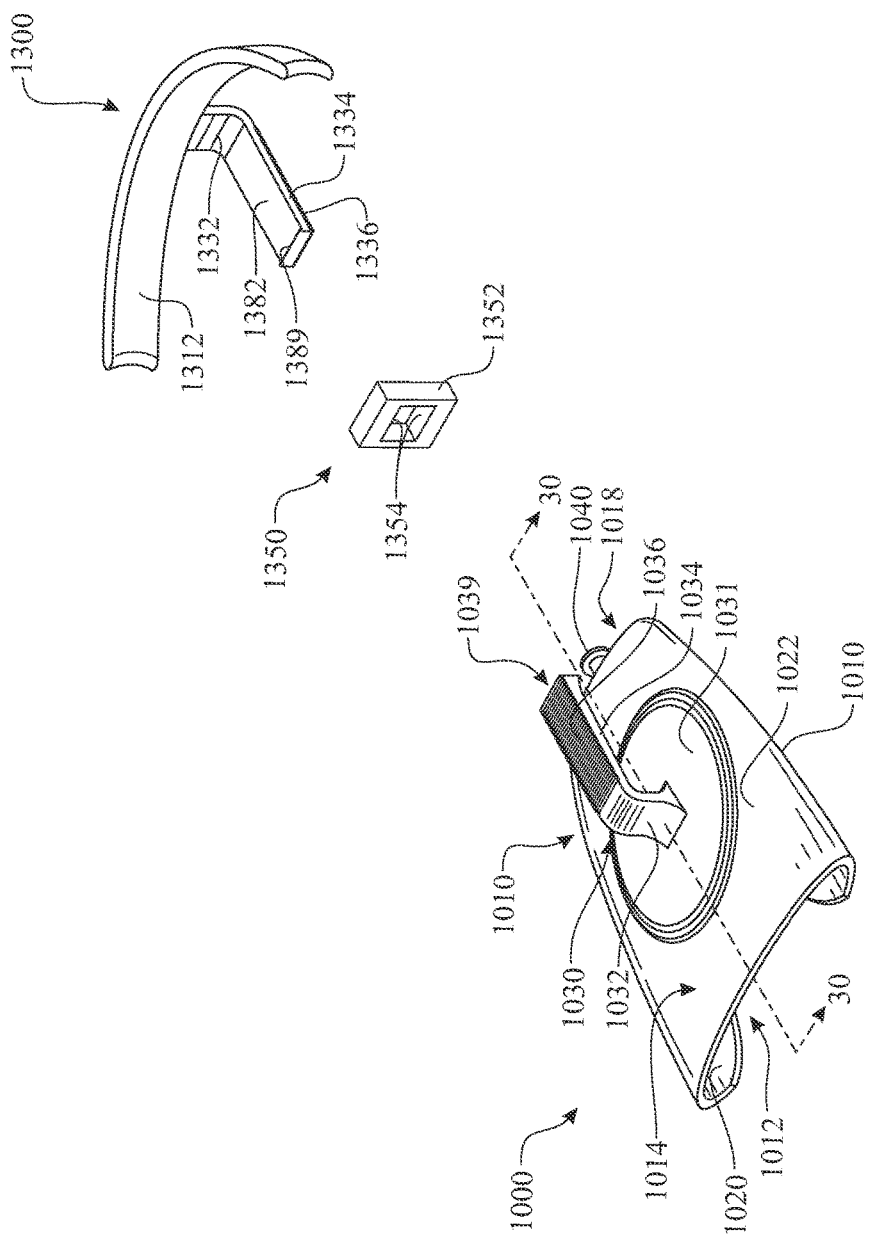
FIG. 29 presents an isometric exploded assembly view of a tongue placement and retention system employing fourth exemplary tongue attachment member, a maxilla lip retention device and a position retaining member, wherein the fourth exemplary tongue attachment member is a variant of the third exemplary tongue attachment member introduced in FIG. 22, wherein a sheath interlock member is assembled to the tongue attachment member body by an overmolded section.
Figure 30:
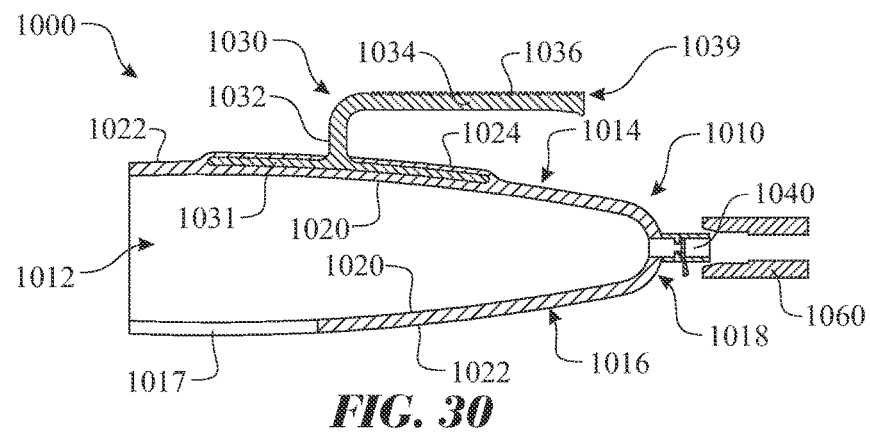
FIG. 30 presents a sectioned view of the fourth tongue attachment member taken along section 30-30 of FIG. 29, wherein the illustration presents a bulb air extraction tube of an air extraction device prior to insertion onto an air extraction valve.
Figure 31:
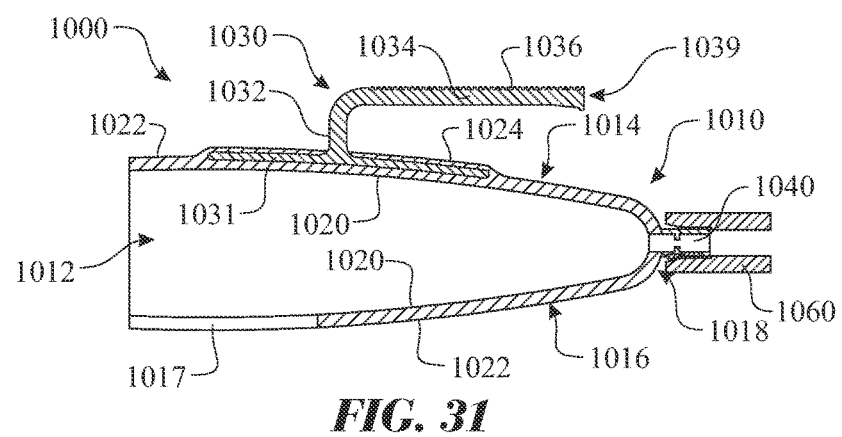
FIG. 31 presents a sectioned view of the fourth tongue attachment member taken along section 30-30 of FIG. 29, wherein the illustration presents the bulb air extraction tube of the air extraction device following insertion onto the air extraction valve.

The maxilla lip retention subassembly 800 can be modified to include a variation of the lip retention subassembly interlock member 830, wherein the modified assembly is referred to as a maxilla lip retention subassembly 900 and is illustrated in FIGS. 26 through 28. Like features of the maxilla lip retention subassembly 900 and maxilla lip retention subassembly 800 numbered the same except preceded by the numeral '9'. The maxilla lip retention subassembly 900 is one exemplary component for use in conjunction with the tongue embracing member 700. The maxilla lip retention subassembly 900 includes a maxilla lip retention positioning arm 930 extending from a lower edge of a lip retention section 910. The maxilla lip retention positioning arm 930 can be designed having any suitable shape to appropriately position the lip retention section 910 when the maxilla lip retention subassembly 900 is attached to the tongue embracing member 700. The exemplary maxilla lip retention positioning arm 930 is shaped to include a positioning arm riser arm 932 extending downward from the lip retention section 910 transitioning into a positioning arm lateral arm 934 which extends rearward and substantially perpendicular to the positioning arm riser arm 932. The maxilla lip retention positioning arm 930 can be provided in any configuration to adjustably and/or detachably mate with the selected design of the sheath interlock member 730.

The positioning arm lateral arm 934 would be positioned parallel to the interlock member engagement segment 734 and secured to one another using a position retaining member 950. The position retaining member 950 can be a separate member or integrated into one of the interlock member engagement segment 734 or the positioning arm lateral arm 934. The position retaining member 950 comprises a position retaining member body 952 formed having a series of walls defining a position retaining member body interior surface 954, wherein the position retaining member body interior surface 954 at least partially circumscribes the combined positioning arm lateral arm 934 and interlock member engagement segment 734. A position retaining member position locking element 956 can be integrated along one or more sides of the position retaining member 950, wherein the position retaining member position locking element 956 releasably engages with at least one of the interlock member positioning feature 736 and notched or ridged surface 936 to secure the maxilla lip retention positioning arm 930 in an axial positional relation with the sheath interlock member 730. The position retaining member position locking element 956 can be designed and operate in conjunction with any locking device known by those skilled in the art.

The exemplary embodiment presents two planar arms arranged in slideable contact with one another. It is understood that one arm can be provided in a form of a channel and the mating arm can be provided in a form of a rail, wherein the rail is slideably assembled within an interior portion of the channel. One of the two members can include a series of recessions that would engage with one or more position locking bosses.

The exemplary maxilla lip retention subassembly 900 is shown in use in FIG. 27. The user can positionally adjust the maxilla lip retention subassembly 900 respective to the tongue embracing member 700 by adjusting the longitudinal relation between the positioning arm lateral arm 934 and the interlock member engagement segment 734. The longitudinal position between the positioning arm lateral arm 934 and the interlock member engagement segment 734 would be retained by the position retaining member 950. The exemplary position retaining member 950 includes a pair of position retaining member position locking element 956, each position retaining member position locking element 956 being located on each side thereof. The position retaining member position locking element 956 engages with each of the interlock member positioning feature 736 and interlocking member contact surface 982 to limit any axial motion between the two arms 982, 934. The tongue embracing member 700 would be secured to the tongue 310 of the patient as previously described. The positioning between the interlock member engagement segment 734 and the positioning arm lateral arm 934 either prior to or subsequent to attachment of the tongue embracing member 700 to the tongue 310. The lip retention section 910 would retain the upper lip 330 of the patient in the desired position. The assembly between the maxilla lip retention subassembly 900 and the tongue embracing member 700 would additionally retain the tongue 310 in a desired position. The lip retention section 910 would be fabricated in a similar manner to the fabrication of the lip retention section 810 as previously described.

A tongue embracing member 1000, illustrated in FIGS. 29 through 33, introduces advantages over the tongue embracing member 700. Like features of the tongue embracing member 1000 and tongue embracing member 700 are numbered the same except preceded by the numeral '10'. The sheath interlock member 1030 is fabricated of a substantially rigid material, such as a rigid plastic. The sheath 1010 is fabricated of a pliant material, such as silicone. The differences in material properties deviates options for manufacturing from a single injection molding process. In the exemplary embodiment, the sheath interlock member 1030 includes a sheath interlock member base 1031 for assembly to the sheath 1010. The sheath interlock member 1030, more specifically, the sheath interlock member base 1031, can be assembled to the sheath 1010 using a two step process. The sheath interlock member 1030 would be fabricated using a first molding process; forming a substantially rigid material into the sheath interlock member 1030. The sheath interlock member 1030 would be assembled to the sheath 1010 by overmolding the sheath interlock member base 1031 onto the dorsal side 1014 of the sheath 1010. A sheath interlock member overmolded retention feature 1024 would encapsulate the sheath interlock member base 1031 over the sheath 1010, or in an alternative, the sheath interlock member base 1031 would be sandwiched between the sheath interlock member overmolded retention feature 1024 and a main body of the sheath 1010. This is best shown in the cross sectioned views illustrated in FIGS. 30 and 31.

The sheath interlock member 1030 includes additional features similar to the sheath interlock member 730 adapted for an adjustable assembly between the sheath interlock member 1030 and a maxilla lip retention device 1300 (introduced in FIGS. 37 through 41). An interlock member riser segment 1032 extends generally perpendicular from an upper surface of the sheath interlock member base 1031. An interlock member engagement segment 1034 extends generally perpendicular to the interlock member riser segment 1032 or generally parallel to the sheath interlock member base 1031, terminating at an interlock member distal or free end 1039. The sheath interlock member 1030 would be oriented having the interlock member engagement segment 1034 extending in a forward direction and located above, parallel to, and in alignment with a longitudinal axis of the sheath 1010. An interlock member positioning feature 1036 can be formed on a surface of the interlock member engagement segment 1034, wherein the surface of the interlock member engagement segment 1034 is designed to engage with a mating surface of a positioning arm lateral segment 1334 (introduced in FIGS. 37 through 41) of the maxilla lip retention positioning arm 1330. Details of the interlock member positioning feature 1036 will be introduced when describing an interlock member positioning feature 1236 of a sheath interlock member 1230 (introduced in FIGS. 37 through 41) later herein.

Figure 32:
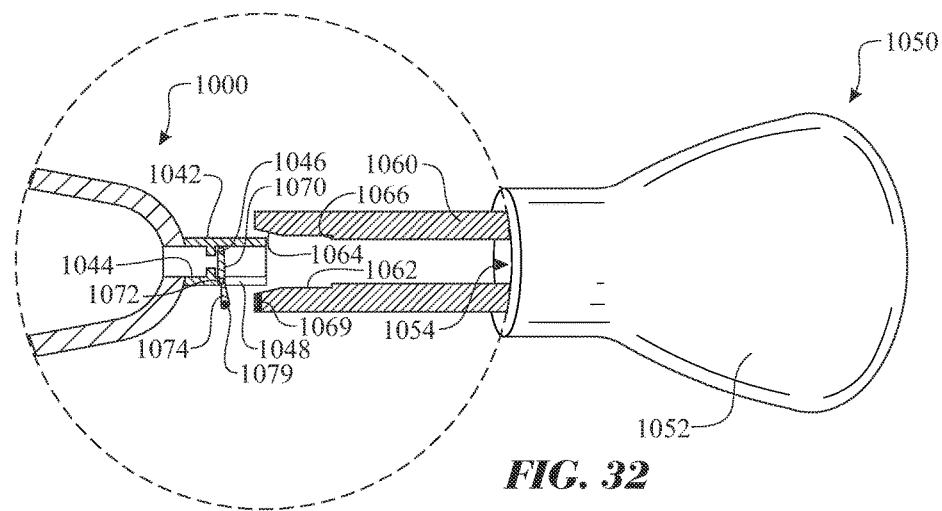
FIG. 32 presents an enlarged, partially sectioned view of the air extraction valve and the associated air removal system, wherein the illustration presents the bulb air extraction tube of the air extraction device prior to insertion onto the air extraction valve.
Figure 33:
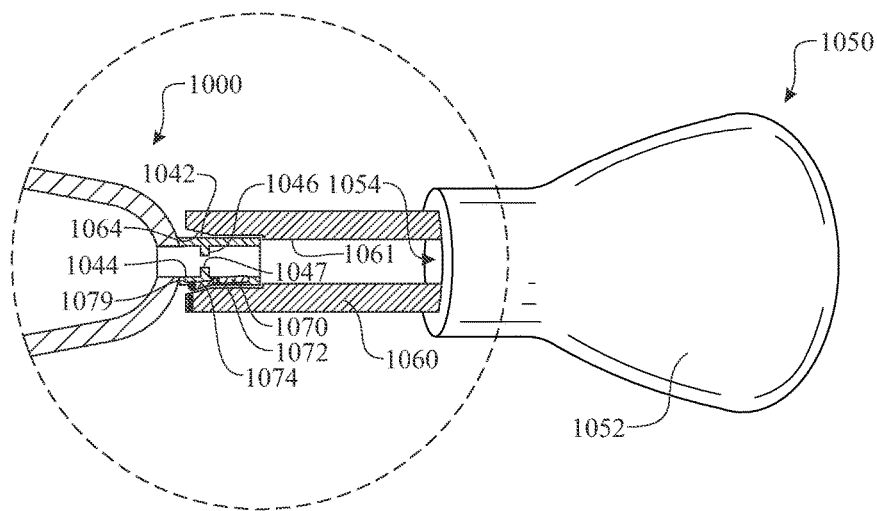
FIG. 33 presents an enlarged, partially sectioned view of the air extraction valve and the associated air removal system, wherein the illustration presents the bulb air extraction tube of the air extraction device following insertion onto the air extraction valve.

The tongue embracing member 1000 introduces a unique air extraction valve 1040, which is best shown in FIGS. 32 and 33. The tongue embracing member 1000 is retained upon the individual's tongue 300 by creating a vacuum in the space between an interior surface 1020 of the sheath 1010 and a tongue surface 302 of the individual's tongue 300. The air extraction valve 1040 must be designed with considerations of the vacuum. A common valve configuration pivots the unidirectional valve flap 142 inward, as shown in FIG. 4. It is noted that the employment of the vacuum could introduce a force that may draw the unidirectional valve flap 142 inward. This could introduce an unwarranted leak through the valve. The air extraction valve 1040 introduces an alternative valve configuration that is adapted with considerations of the implied vacuum forces.

The air extraction valve 1040 includes a valve flap 1070 that is pivotally assembled to the primary tubular structure of the air extraction valve 1040 by a valve hinge pin 1072. The valve flap 1070 is designed to pivot outward, or away from the vacuum cavity or tongue receiving cavity 1012 of the sheath 1010. The valve flap 1070 seats against an air extraction valve seal flange 1046 provided annually about an air extraction valve interior surface 1044 of the primary tubular structure of the air extraction valve 1040. The valve flap 1070 toggles between a closed configuration (FIG. 32), sealing an air extraction valve seal flange orifice 1047 and an opened configuration (FIG. 33), exposing the air extraction valve seal flange orifice 1047 for airflow therethrough.

A valve operational handle 1074 extends outward from the valve flap 1070. The valve flap 1070 and the valve operational handle 1074 are preferably located on opposite sides of the valve hinge pin 1072. The valve operational handle 1074 is preferably located externally to the primary tubular structure of the air extraction valve 1040, while the valve flap 1070 is located within an interior of the primary tubular structure of the air extraction valve 1040. The valve flap 1070 is shaped and sized to seal against the air extraction valve seal flange 1046 within the interior of the primary tubular structure of the air extraction valve 1040.

Details of an air extraction device 1050 in use are presented in FIGS. 32 and 33. The air extraction device 1050 includes a bulb air extraction tube 1060 extending outward from and in fluid communication with a bulb air extraction orifice 1054 of an air extraction bulb 1052. The air extraction bulb 1052 is fabricated of a pliant material, such as rubber, silicone, soft plastic, and the like. The pliant material enables compression of the air extraction bulb 1052 to expel air from within an interior thereof. Elastic properties of the pliant material enable the air extraction bulb 1052 to return to a natural shape. As the air extraction bulb 1052 returns from a collapsed condition to a natural shape, the air extraction bulb 1052 draws air through an interior of the bulb air extraction tube 1060, wherein the interior is defined by a bulb air extraction tube hollow interior 1061. The air drawn by the air extraction bulb 1052 removes air from the tongue receiving cavity 1012 generating a vacuum.

The illustrations in FIGS. 32 and 33 additionally present operation of the air extraction valve 1040. The bulb air extraction tube 1060 includes features to rotate the valve flap 1070, exposing the air passageway defined by the air extraction valve seal flange orifice 1047. An air extraction tube lead-in 1064 is formed at a distal end of the bulb air extraction tube hollow interior 1061. The air extraction tube lead-in 1064 can be a linear chamfer, a curved chamfer or of any other suitable shape. The air extraction tube lead-in 1064 extends between an initial opening having a diameter that is greater than a diameter of an air extraction valve exterior surface 1042 of the tongue bladder air extraction tube and a diameter of an air extraction tube seal surface 1062, wherein the air extraction tube seal surface 1062 is of a shape and size to create a snug, airtight seal about the air extraction valve exterior surface 1042 of the tongue bladder air extraction tube. An optional valve insertion stop seat 1066 can be formed between the air extraction tube seal surface 1062 and a balance of the bulb air extraction tube hollow interior 1061, wherein the valve insertion stop seat 1066 is a slight reduction in an interior diameter providing a stop placed against a distal end of the tongue bladder air extraction tube. The bulb air extraction tube hollow interior 1061 ensures against over insertion of the tongue bladder air extraction tube into the air extraction tube seal surface 1062 and could provide an additional seal between the tongue bladder air extraction tube and the bulb air extraction tube 1060. As the bulb air extraction tube 1060 is slideably placed over the tongue bladder air extraction tube, the surface of the bulb air extraction tube 1060 engages with the valve operational handle 1074. The relative motion between the tongue bladder air extraction tube and the air extraction valve 1040 pushes the valve operational handle 1074 forward, causing the valve assembly to pivot or rotate accordingly about the valve hinge pin 1072. The rotation pivots the valve flap 1070 away from the air extraction valve seal flange 1046, exposing the air extraction valve seal flange orifice 1047 defined by the air extraction valve seal flange 1046, and enabling air to pass therethrough. As the tongue bladder air extraction tube is slideably positioned onto the air extraction valve exterior surface 1042, the surfaces of the air extraction tube seal surface 1062 and the air extraction valve exterior surface 1042 contact one another forming an airtight seal. The user would compress the air extraction bulb 1052 either prior to the slideable insertion process or subsequent to the slideable insertion process. The compression forces air from the interior of the air extraction bulb 1052. This is in preparation for a step of drawing a vacuum from the tongue receiving cavity 1012. Once the air extraction device 1050 is secured to the air extraction valve 1040, with the valve flap 1070 in an open configuration, the user would release the applied compression, the air extraction bulb 1052 expands, returning to its original shape, and the expansion draws air from the tongue receiving cavity 1012, through an air extraction valve interior surface 1044 of the tongue bladder air extraction tube, through the air extraction valve seal flange orifice 1047, and into the bulb air extraction orifice 1054 creating a vacuum between the interior surface 1020 and the tongue surface 302. The vacuum generated retains the sheath 1010 in position on the tongue 300 of the user. The sheath interlock member 1030 would be assembled to a maxilla lip retention device 1300 (FIGS. 37 through 41) to draw the tongue 300 forward within the user's mouth to a desired position and retain the tongue 300 in the desired position. Details of this process will be described later herein.

The air extraction valve 1040 can include one or more features to aid in returning the valve flap 1070 to a sealed position. One such feature could be a biasing member, such as a cantilever spring. A second feature, presented in FIGS. 32 and 33, employs a magnetic force. One portion of a magnetically attracting pair of materials is a valve return control magnet 1079. The valve return control magnet 1079 is carried by the valve operational handle 1074. A second portion of a magnetically attracting pair of materials is a valve return control magnet 1069. The valve return control magnet 1069 is carried by a distal end of the bulb air extraction tube 1060. The magnetic attraction between the valve return control magnet 1069 and the valve return control magnet 1079 draws the valve operational handle 1074 away from the sheath 1010 as the bulb air extraction tube 1060 is separated from the tongue bladder air extraction tube, causing the valve operational handle 1074 to rotate, drawing the valve flap 1070 into a closed configuration against the air extraction valve seal flange 1046. The vacuum generated within the tongue receiving cavity 1012 retains the valve flap 1070 in a closed configuration. Although the exemplary embodiment employs a magnetic attraction, it is understood that any temporary coupling can be utilized, including an adhesive grip, a mechanical engagement such as a snap feature, and the like.

An air extraction valve clearance 1048 can be formed within the tongue bladder air extraction tube, wherein the air extraction valve clearance 1048 provides a clearance for the valve flap 1070 as shown in FIG. 33. Since the air extraction valve clearance 1048 is formed on a portion of the tongue bladder air extraction tube outside of the airtight boundary defined by the tongue receiving cavity 1012 and the air extraction valve 1040.

In the tongue embracing member 1000, the sheath interlock member 1030 is assembled to the sheath 1010 by an overmolding process. The sheath interlock member 1030 can be assembled to the sheath 1010 using any suitable method. A tongue embracing member 1100 presents an alternative configuration for assembling a sheath interlock member 1130 to a sheath 1110, as shown in FIGS. 34 through 36. The tongue embracing member 1100 is similar to the tongue embracing member 1000, whereby the distinguishing features are described herein. Like features of the tongue embracing member 1100 and tongue embracing member 1000 are numbered the same except preceded by the numeral '11'. A sheath interlock member base 1131 of the sheath interlock member 1130 is shaped to contour to a surface associated with a dorsal side 1114 of a sheath 1110 of the tongue embracing member 1100. The sheath interlock member base 1131 is defined by a peripheral boundary, more specifically a pair of sheath interlock member base longitudinal edges 1133 and a pair of sheath interlock member base lateral edges 1135. An arrangement of channels 1124, 1126 is formed on the portion of an exterior surface 1122 associated with the dorsal side 1114 of the sheath 1110, wherein the arrangement of channels 1124, 1126 are shaped and sized to receive and retain the sheath interlock member base 1131 on the exterior surface 1122 of the sheath 1110. The arrangement of channels 1124, 1126 includes a pair of lateral channels 1126 transversely arranged upon the exterior surface 1122 and a longitudinal channel 1124 extending between like ends of the pair of lateral channel 1126, wherein the first channel segment 1126, the third channel segment 1124 and the second channel segment 1126 collectively form a "U" shaped channel. Each lateral channel 1126 defines a lateral channel groove 1125. The longitudinal channel 1124 defines a longitudinal channel groove 1123. The sheath interlock member base lateral edge 1135 slides into the lateral channel groove 1125. The lateral channel 1126 constrains the sheath interlock member 1130 against any longitudinal movement. The sheath interlock member base 1131 slides into the longitudinal channel groove 1123. The longitudinal channel 1124 provides an insertion stop in a transverse direction to ensure proper alignment between an interlock member engagement segment 1134 and a longitudinal centerline of the sheath 1110. This configuration enables low cost manufacturing of the tongue embracing member 1100 compared to the costs of a two part overmolding process by avoiding a step of inserting the sheath interlock member 1030 into the mold cavity used for fabricating the sheath 1010 and the additional machine costs for the additional movements of mold sections to accommodate the inserted sheath interlock member 1030.

As previously described, the tongue embracing member 1100 is temporarily secured to the individual's tongue 300 by created a vacuum between the interior surface 1120 and the tongue surface 302. The tongue embracing member 1100 introduces a sheath tongue sealing ridge 1121, wherein the preferred design includes a sheath tongue sealing ridge 1121 circumscribing a peripheral edge of the interior surface 1120. The sheath tongue sealing ridge 1121 acts as a gasket, enhancing the seal between the interior surface 1120 and the tongue surface 302 when subjected to the vacuum.

Figures 37, 38, 39:
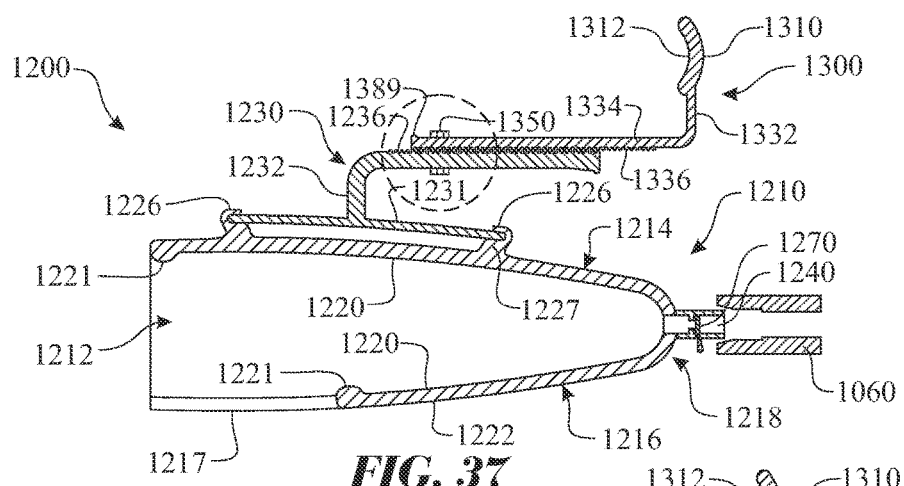
FIG. 37 presents a sectioned view of the sixth tongue attachment member, wherein the sixth exemplary tongue attachment member is a variant of the fifth exemplary tongue attachment member as shown in FIG. 35, wherein a sheath interlock member is slideably assembled to a channel formed having an arrangement spatially above the dorsal side of the tongue attachment member body, the valve shown in a closed configuration and a maxilla lip retention device shown in a slideably adjustable, retracted configuration.
FIG. 38 presents a sectioned view of the sixth tongue attachment member, the illustration being similar to the illustration presented in FIG. 37, wherein the valve shown in an open configuration and a maxilla lip retention device shown in a slideably adjustable, extended configuration.
FIG. 39 presents a sectioned view of the sixth tongue attachment member, the illustration being similar to the illustration presented in FIGS. 37 and 38, wherein the valve shown in an closed configuration and a maxilla lip retention device shown in a secured or locked configuration.

In the tongue embracing member 1100, the sheath interlock member base 1131 is assembled to the sheath 1110 by sliding the sheath interlock member base 1131 into recessions 1123, 1125 formed by channels 1124, 1126. The channel configuration positions a lower surface of the sheath interlock member base 1131 against the exterior surface 1122 of the sheath 1110. In certain circumstance, this arrangement can potentially cause the interior surface 1120 to dislodge from the tongue surface 302 of the tongue 300, resulting in a breach of the vacuum therein. A tongue embracing member 1200 presents an alternative channel configuration to accommodate this potential risk by including a channel riser feature 1227, as shown in FIGS. 37 through 39. The tongue embracing member 1200 is similar to the tongue embracing member 1100, whereby the distinguishing feature is the channel riser feature 1227. Like features of the tongue embracing member 1200 and tongue embracing member 1100 are numbered the same except preceded by the numeral '12'. The channel riser feature 1227 introduces a space between the exterior surface 1222 of a sheath 1210 and a lower surface of a sheath interlock member base 1231 of a sheath interlock member 1230. Properties of the channel riser feature 1227 introduces flexure thereof, reducing transfer of any torsional forces generated by a motion of the maxilla lip retention device 1300 translating through the sheath interlock member 1230 onto the sheath 1210. This reduction in transfer of any generated torsional forces reduces any potential risk of breaching the vacuum forces between the interior surface 1220 and the tongue surface 302 of the tongue 300.

Figure 40:
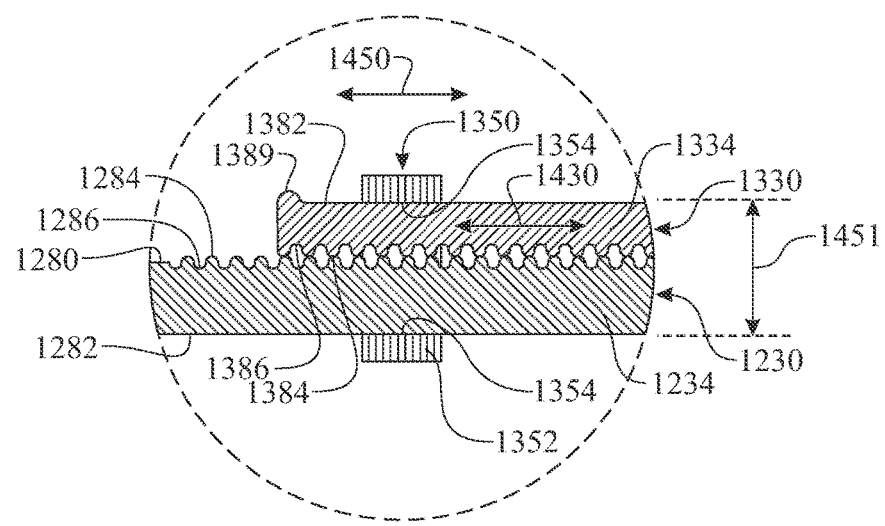
FIG. 40 presents a magnified sectioned view detailing a positioning control system used to toggle between an adjustable configuration and a locked configuration between a sheath interlock member arm of the sheath interlock member and a maxilla lip retention positioning arm of a maxilla lip retention device, the illustration presenting the interlocking assembly in a slideably adjustable configuration.
Figure 41:
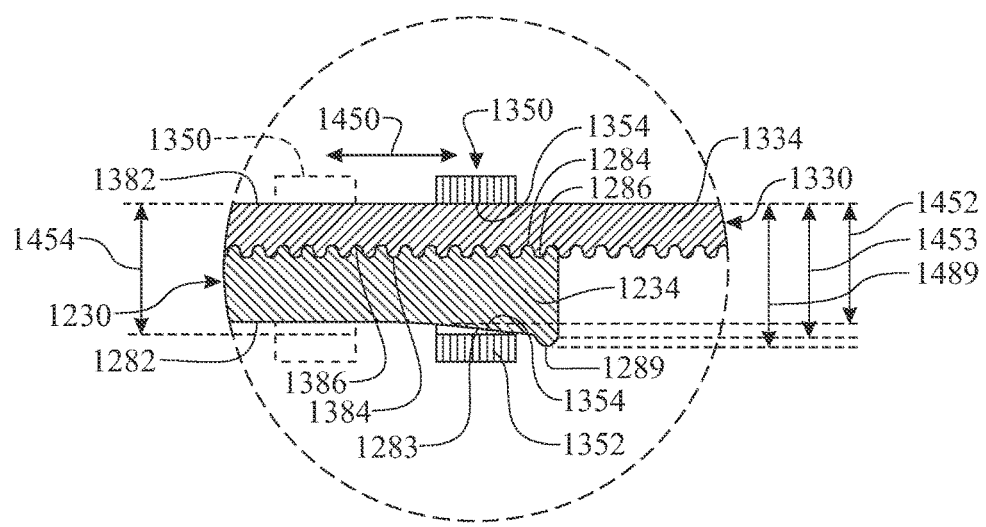
FIG. 41 presents a magnified sectioned view introduced in FIG. 40, the illustration presenting the interlocking assembly in a locked or motion restricted configuration.

The tongue embracing member 1200 is designed to draw the tongue 300 of the user forward. This positioning retention system can be employed for sleep apnea, during a surgical procedure to ensure the patient's tongue 300 does not become lodge in the patient's throat. The positioning retention system utilizes a position adjusting system created by features of the sheath interlock member 1230, features of the maxilla lip retention positioning arm 1330, and a position retaining member 1350. The interlock member positioning feature 1236 of the interlock member engagement segment 1234 can be of any suitable grip enhancing feature. This can include a friction enhancing surface (adding texture, adding a material having a higher coefficient of friction, and the like), forming the surface of the interlock member engagement segment 1234 into a desired shape (such as a series of interlock member locking surface projection (peak) 1284 and interlock member locking surface recession (valley) 1286 as illustrated in FIGS. 40 and 41) and the like. In the exemplary embodiment, the interlock member positioning feature 1236 includes a series of interlock member locking surface projection (peak) 1284 and interlock member locking surface recession (valley) 1286. The interlock member locking surface projections (peaks) 1284 and interlock member locking surface recessions (valleys) 1286 can be formed in any design to matingly engage with like positioning arm locking surface projections (peaks) 1384 and positioning arm locking surface recessions (valleys) 1386 formed on a mating surface of the positioning arm lateral segment 1334. In the exemplary embodiment, the interlock member locking surface projections (peaks) 1284 and interlock member locking surface recessions (valleys) 1286 and the mating positioning arm locking surface projections (peaks) 1384 and positioning arm locking surface recessions (valleys) 1386 are linear in formation and equally spaced arranged. The interlock member locking surface projections (peaks) 1284 and interlock member locking surface recessions (valleys) 1286 and the mating positioning arm locking surface projections (peaks) 1384 and positioning arm locking surface recessions (valleys) 1386 can be formed at any angle respective to a longitudinal axis of the respective interlock member engagement segment 1234, positioning arm lateral segment 1334. In the exemplary embodiment, the interlock member locking surface projections (peaks) 1284 and interlock member locking surface recessions (valleys) 1286 and the mating positioning arm locking surface projections (peaks) 1384 and positioning arm locking surface recessions (valleys) 1386 are perpendicular to a longitudinal axis of the respective interlock member engagement segment 1234, positioning arm lateral segment 1334. More specifically, the interlock member locking surface projections (peaks) 1284 and interlock member locking surface recessions (valleys) 1286 and the mating positioning arm locking surface projections (peaks) 1384 and positioning arm locking surface recessions (valleys) 1386 are linear, oriented substantially parallel to one another, and equally spaced arranged.

Although the interlock member locking surface projections (peaks) 1284 and interlock member locking surface recessions (valleys) 1286 and the mating positioning arm locking surface projections (peaks) 1384 and positioning arm locking surface recessions (valleys) 1386 are shown as having a linear arrangement, it is understood that the interlock member locking surface projections (peaks) 1284 and interlock member locking surface recessions (valleys) 1286 and the mating positioning arm locking surface projections (peaks) 1384 and positioning arm locking surface recessions (valleys) 1386 can be of any suitable design, including a cross hatching, a series of bosses and embosses, a series of dimples and recessions, and the like.

The interlock member engagement segment 1234 and the associated positioning arm lateral segment 1334 are assembled together orienting mating surfaces contacting one another, as best shown in FIGS. 40 and 41.

The position retaining member 1350 at least partially circumscribes an external periphery defined by an assembly of the sheath interlock member arm 1234 and the maxilla lip retention subassembly segment 1334. The position retaining member 1350 includes a position retaining member body 1352 preferably shaped as a tubular member. The position retaining member 1350 can be formed having a tubular rectangle shape, a tubular oblong shape, an elliptical shape, and the like, wherein the preferred shape would mimic the cross sectional shape of the assembly of the sheath interlock member arm 1234 and the maxilla lip retention subassembly segment 1334. It is understood that the position retaining member 1350 can be fabricated in any suitable cross sectional shape, including a "C" channel shape, a "U" channel shape, any tubular shape, an "I" beam shape, or having any other suitable cross sectional design.

An interior distance 1454 spanning between an interior transverse or upper surface 1354 and an interior opposite transverse or lower surface 1354 of the position retaining member 1350 is sized enabling a sliding motion between the sheath interlock member arm 1234 and the maxilla lip retention subassembly segment 1334 when positioned at a location of the assembly having a narrow thickness (illustrated as the position retaining member 1350 presented in broken lines on FIG. 41) and restraining any sliding motion between the sheath interlock member arm and the maxilla lip retention subassembly arm when positioned at a location of the assembly having a wider thickness (illustrated as the position retaining member 1350 presented in solid lines on FIG. 41).

The position retaining member internal span 1454 would be of a dimension enabling separation between the interlock member engagement segment 1234 and the positioning arm lateral segment 1334, thus disengaging the interlock member positioning feature 1236 (the interlock member locking surface projection (peak) 1284 and the interlock member locking surface recession (valley) 1286) and the interlock member positioning feature 1336 (the positioning arm locking surface projection (peak) 1384 and the positioning arm locking surface recession (valley) 1386) from one another, enabling a sliding motion 1430. The interlock member engagement segment 1234 and the positioning arm lateral segment 1334 separates sufficiently enabling the interlock member locking surface projection (peak) 1284 and the positioning arm locking surface projection (peak) 1384 to slide over one another. The minimum dimension is identified as a teeth disengaged configuration assembly thickness 1451 (the distance between the interlock member position retaining member support surface 1282 and the position retaining member support surface 1382 when the interlock member engagement segment 1234 and the positioning arm lateral segment 1334 are separated from one another in a positionable configuration), as shown in FIG. 40. The position retaining member internal span 1454 must be at least equal to or greater than the teeth disengaged configuration assembly thickness 1451.

The sliding motion 1430 enables positioning of the interlock member engagement segment 1234 and the positioning arm lateral segment 1334 relative to one another. This positioning properly locates the sheath 1210, thus properly positioning and retaining the tongue 300 of the user as desired. It is noted that the design of the interlock member locking surface projection (peak) 1284 and the interlock member locking surface recession (valley) 1286 as well as the positioning arm locking surface projection (peak) 1384 and the positioning arm locking surface recession (valley) 1386 define a pitch, or the limitations for the change in a locked position. The finer the pitch (smaller the spatial gap between like features), the greater the adjustability of the position between the interlock member engagement segment 1234 and the positioning arm lateral segment 1334.

Once the interlock member engagement segment 1234 and the positioning arm lateral segment 1334 are located in a desired position respective to one another, they are brought together, seating the interlock member locking surface projection (peak) 1284 into the respective positioning arm locking surface recession (valley) 1386 and similarly, seating the positioning arm locking surface projection (peak) 1384 into the respective interlock member locking surface recession (valley) 1286. This reduces the dimension between the interlock member position retaining member support surface 1282 and the position retaining member support surface 1382 from the teeth disengaged configuration assembly thickness 1451 to a teeth engaged configuration assembly thickness 1452 (the distance between the interlock member position retaining member support surface 1282 and the position retaining member support surface 1382 when the interlock member engagement segment 1234 and the positioning arm lateral segment 1334 are brought together in a locked configuration), introduced in FIG. 41. Once the interlock member engagement segment 1234 and the positioning arm lateral segment 1334 are brought together, seating the interlock member locking surface projection (peak) 1284 into the respective positioning arm locking surface recession (valley) 1386 and similarly, seating the positioning arm locking surface projection (peak) 1384 into the respective interlock member locking surface recession (valley) 1286, the position retaining member 1350 is repositioned in accordance with a position retaining member sliding motion 1450 from the adjustment position (shown in broken line) to a locked or retention position (shown in solid line). The position retaining member 1350 is moved into a region of the sheath interlock member 1230 having an interlock member thickness wedge shaped segment 1283. The interlock member thickness wedge shaped segment 1283 is formed along a segment of at least one of the sheath interlock member arm 1234 and the maxilla lip retention subassembly segment 1334. The interlock member thickness wedge shaped segment 1283 is formed as a changing thickness of the sheath interlock member arm 1234 (as shown) and/or the maxilla lip retention subassembly segment 1334 defining a tapering distal or outer surface. The interlock member thickness wedge shaped segment 1283 creates a wedge, increasing a dimension between opposite outer surfaces 1382, 1283, (referenced as a teeth engaged configuration assembly wedge section thickness 1453), securing the position retaining member 1350 in position. The position retaining member 1350 retains engagement between the interlock member positioning feature 1236 and the interlock member positioning feature 1336, thus retaining the positional relationship between the interlock member engagement segment 1234 and the positioning arm lateral segment 1334. A position retaining member retention feature 1289 can be formed at a distal end of the interlock member engagement segment 1234. The introduction of the position retaining member retention feature 1289 defines a position retaining member retention thickness 1489. The position retaining member retention thickness 1489 is greater than the position retaining member internal span 1454, thus keeping the position retaining member 1350 from becoming separated from the assembly. Similarly, a position retaining member retention feature 1389 can be formed at a distal end of the positioning arm lateral segment 1334. The position retaining member retention feature 1389 provides the same function as the position retaining member retention feature 1289, but at an opposite end of the assembly, thus ensuring against separation of the position retaining member 1350 from the assembly.

As previously stated, the tongue positioning retention system can be employed for any of a number of applications that would benefit placement and retention of the individual's tongue 300. This includes sleep apnea; during any medical procedure, such as those requiring conscience sedation anesthesia; or any other application to ensure the patient's tongue 300 does not become lodge in the patient's throat, and the like.

Although the illustrations present versions of tongue embracing members having different features, it is understood that features of any exemplary tongue embracing members can be adapted to any of the other exemplary tongue embracing members.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

REF. NO. DESCRIPTION 100 tongue attachment subassembly
110 sheath
112 tongue receiving cavity
114 dorsal side
116 ventral side
117 tongue base clearance
118 sheath distal end
120 exterior surface
122 tongue engagement surface
130 sheath interlock member
132 interlock ridge
134 interlock tooth
136 interlock tooth receptacle
138 interlock base portion
140 air extraction valve
142 unidirectional valve flap
144 unidirectional valve seal
146 unidirectional valve orifice
150 air extraction device
152 air extraction bulb
154 air extraction pipette
200 maxilla attachment device
210 maxilla tray
220 maxilla tray's attachment side
222 maxilla tray's interlock side
230 tray interlock member
234 interlock tooth
236 interlock tooth receptacle
300 individual's tongue
302 tongue surface
304 gap
306 tongue base
310 extended tongue
320 maxilla (upper jaw)
322 mandible (lower jaw)
330 upper lip
400 sleep apnea control method flow diagram
402 obtain sleep apnea control device step
404 place tongue embracing member upon individual's tongue step
406 extract air from between the tongue receiving cavity of the tongue embracing member and the individual's tongue step
408 place maxilla attachment device onto the individual's maxilla step
410 extend individual's tongue forward step
412 engage sheath interlock member and tray interlock member together step
414 enjoy nights sleep step
416 remove vacuum from between the tongue receiving cavity and the individual's tongue step
418 remove the tongue embracing member from the individual's tongue step
420 remove maxilla attachment device from individual's maxilla step
500 tongue embracing member
510 sheath
512 tongue receiving cavity
514 dorsal side
516 ventral side
517 tongue base clearance
518 sheath distal end
530 sheath interlock member
540 air extraction valve
560 bladder exterior wall
562 bladder interior wall
564 bladder air chamber
600 tongue embracing member
610 sheath
612 tongue receiving cavity
614 dorsal side
616 ventral side
617 tongue base clearance
618 sheath distal end
620 interior wall
622 exterior wall
630 sheath interlock member
634 interlock pin
636 interlock tooth receptacle
638 interlock base portion
640 air extraction valve
650 air extraction device
652 air extraction bulb
700 tongue embracing member
710 sheath
712 tongue receiving cavity
714 dorsal side
716 ventral side
717 tongue base clearance
718 sheath distal end
720 interior surface
722 exterior surface
730 sheath interlock member
732 interlock member riser segment
734 interlock member engagement segment
736 interlock member positioning feature
740 air extraction valve
750 air extraction device
752 air extraction bulb
800 maxilla lip retention device
810 lip retention section
812 lip retention surface
820 maxilla lip retention positioning arm
822 positioning arm lateral arm
824 positioning arm riser arm
830 tray interlock member
834 interlocking member contact surface
836 interlock pin receptacle
838 interlock base portion
900 maxilla lip retention device
910 lip retention section
912 lip retention surface
930 maxilla lip retention positioning arm
932 positioning arm riser arm
934 positioning arm lateral arm
936 notched or ridged surface
950 position retaining member
952 position retaining member body
954 position retaining member body interior surface
956 position retaining member position locking element
982 interlocking member contact surface
1000 tongue embracing member
1010 sheath
1012 tongue receiving cavity
1014 dorsal side
1016 ventral side
1017 tongue base clearance
1018 sheath distal end 1020 interior surface
1022 exterior surface
1024 sheath interlock member overmolded retention feature
1030 sheath interlock member
1031 sheath interlock member base
1032 interlock member riser segment
1034 interlock member engagement segment
1036 interlock member positioning feature
1039 interlock member distal end
1040 air extraction valve
1042 air extraction valve exterior surface
1044 air extraction valve interior surface
1046 air extraction valve seal flange
1047 air extraction valve seal flange orifice
1048 air extraction valve clearance
1050 air extraction device
1052 air extraction bulb
1054 bulb air extraction orifice
1060 bulb air extraction tube
1061 bulb air extraction tube hollow interior
1062 air extraction tube seal surface
1064 air extraction tube lead-in
1066 valve insertion stop seat
1069 valve return control magnet
1070 valve flap
1072 valve hinge pin
1074 valve operational handle
1079 valve return control magnet
1100 tongue embracing member
1110 sheath
1112 tongue receiving cavity
1114 dorsal side
1116 ventral side
1117 tongue base clearance
1118 sheath distal end
1120 interior surface
1121 sheath tongue sealing ridge
1122 exterior surface
1123 longitudinal channel groove
1124 longitudinal channel
1125 lateral channel groove
1126 lateral channel
1130 sheath interlock member
1131 sheath interlock member base
1132 interlock member riser segment
1133 sheath interlock member base longitudinal edge
1134 interlock member engagement segment
1135 sheath interlock member base lateral edge
1136 interlock member positioning feature
1139 interlock member distal end
1140 air extraction valve
1170 valve flap
1200 tongue embracing member
1210 sheath
1212 tongue receiving cavity
1214 dorsal side
1216 ventral side
1217 tongue base clearance
1218 sheath distal end
1220 interior surface
1221 sheath tongue sealing ridge
1222 exterior surface
1223 longitudinal channel groove
1224 longitudinal channel
1225 lateral channel groove
1226 lateral channel
1227 channel riser feature
1230 sheath interlock member
1231 sheath interlock member base
1232 interlock member riser segment
1233 sheath interlock member base longitudinal edge
1234 interlock member engagement segment
1235 sheath interlock member base lateral edge
1236 interlock member positioning feature
1239 interlock member distal end
1240 air extraction valve
1270 valve flap
1282 interlock member position retaining member support surface
1283 interlock member thickness wedge shaped segment
1284 interlock member locking surface projection (peak)
1286 interlock member locking surface recession (valley)
1289 position retaining member retention feature
1300 maxilla lip retention device
1310 lip retention section
1312 lip retention surface
1330 maxilla lip retention positioning arm
1332 positioning arm riser segment
1334 positioning arm lateral segment
1336 interlock member positioning feature
1350 position retaining member
1352 position retaining member body
1354 position retaining member body interior surface
1382 position retaining member support surface
1384 positioning arm locking surface projection (peak)
1386 positioning arm locking surface recession (valley)
1389 position retaining member retention feature
1430 sliding motion
1450 position retaining member sliding motion
1451 teeth disengaged configuration assembly thickness
1452 teeth engaged configuration assembly thickness
1453 teeth engaged configuration assembly wedge section thickness
1454 position retaining member internal span
1489 position retaining member retention thickness

What is claimed is:

1. A tongue positioning and retention system, comprising:
a tongue embracing member comprising:
a sheath shaped to conform to a surface of a tongue of an individual, the sheath having a tongue receiving cavity defining an opening for receiving the individual's tongue provided at a proximal end thereof, the sheath having an orientation defined by a dorsal side and a ventral side, and
a sheath interlock member comprising a sheath interlock member riser segment extending upward from the dorsal side of the sheath, continuing with an interlock member engagement segment extending in a direction away from the opening for receiving the individual's tongue; and
a maxilla lip retention subassembly comprising:
a lip retention section having an arched shape, sized to follow a contour of an exterior of a maxilla lip of the individual,
a maxilla lip retention positioning arm extending from the lip retention section, the maxilla lip retention positioning arm comprising a maxilla lip retention positioning arm lateral segment, the maxilla lip retention positioning arm lateral segment extending in a direction radially inward from a concave surface of the arched shape,
a position retaining member comprising:
a body comprising at least one feature adapted to aid in retaining the sheath interlock member engagement segment and the maxilla lip retention positioning arm lateral segment in position relative to one another, wherein the sheath interlock member engagement segment and the maxilla lip retention positioning arm lateral segment are positionably adjustable respective to one another along a longitudinal axis defined by each of the sheath interlock member engagement segment and the maxilla lip retention positioning arm lateral segment, wherein the position retaining member is assembled on the interlock member engagement segment and the maxilla lip retention positioning arm lateral segment between the sheath interlock member riser segment and the lip retention section, wherein when interlocked and installed, the tongue positioning and retention system retains the lip retention section in engagement with the individual's maxilla lip, maintaining the tongue embracing member in position, which maintains the individual's tongue in a desired position.

2. A tongue positioning and retention system as recited in claim 1, the position retaining member further comprising:
the body having an upper segment defining an interior upper surface,
a lower segment defining an interior lower surface, and
an intermediary segment joining the upper segment and the lower segment together,
wherein a distance between the interior upper surface and the interior lower surface defines a position retaining member internal span,
wherein the position retaining member internal span retains the sheath interlock member engagement segment and the maxilla lip retention positioning arm lateral segment in position respective to one another.

3. A tongue positioning and retention system as recited in claim 1, the sheath interlock member engagement segment further comprises a sheath interlock member positioning surface; and
the maxilla lip retention positioning arm lateral segment further comprises a maxilla lip lateral segment positioning surface,
wherein the sheath interlock member positioning surface and the maxilla lip lateral segment positioning surface are assembled contacting one another.

4. A tongue positioning and retention system as recited in claim 3, wherein at least one of the sheath interlock member positioning surface and the maxilla lip lateral segment positioning surface include a friction enhancing surface texture.

5. A tongue positioning and retention system as recited in claim 3, wherein the sheath interlock member positioning surface and the maxilla lip lateral segment positioning surface include a friction enhancing surface texture each include interlocking mechanical features.

6. A tongue positioning and retention system as recited in claim 3, wherein the sheath interlock member positioning surface and the maxilla lip lateral segment positioning surface include a friction enhancing surface texture each include a series of interlocking projections and recessions.

7. A tongue positioning and retention system as recited in claim 1,
wherein at least one of:
(a) the sheath interlock member engagement segment includes a wedge shaped feature, and
(b) the maxilla lip retention positioning arm lateral segment includes a wedge shaped feature.

8. A tongue positioning and retention system as recited in claim 7,
wherein the wedge shaped feature is formed having a smaller dimension and a larger dimension, the wedge shaped feature oriented locating the larger dimension closer to a free end and the smaller dimension being located closer to an attached end of the at least one of (a) the sheath interlock member engagement segment and (b) the maxilla lip retention positioning arm lateral segment.

9. A tongue positioning and retention system, comprising:
a tongue embracing member comprising:
a sheath shaped to conform to a surface of a tongue of an individual, the sheath having a tongue receiving cavity defining an opening for receiving the individual's tongue provided at a proximal end thereof, the sheath having an orientation defined by a dorsal side and a ventral side, and
a sheath interlock member extending outward from the dorsal side of the sheath, the sheath interlock member comprising a sheath interlock member riser segment extending upward from the dorsal side of the sheath, continuing with an interlock member engagement segment extending in a direction away from the opening for receiving the individual's tongue, the sheath interlock member engagement segment including a sheath interlock member positioning surface; and
a maxilla lip retention subassembly comprising:
a lip retention section having an arched shape, sized to follow a contour of an exterior surface of a maxilla lip of the individual,
a maxilla lip retention positioning arm extending from the lip retention section, the maxilla lip retention positioning arm comprising a maxilla lip retention positioning arm lateral segment, the maxilla lip retention positioning arm lateral segment extending in a direction inward from a concave surface of the arched shape, the maxilla lip retention positioning arm lateral segment including a maxilla lip lateral segment positioning surface,
a position retaining member comprising:
a body comprising at least one feature adapted to aid in retaining the sheath interlock member engagement segment and the maxilla lip retention positioning arm lateral segment in position relative to one another,
wherein the sheath interlock member positioning surface and the maxilla lip lateral segment positioning surface are assembled contacting one another,
wherein the sheath interlock member engagement segment and the maxilla lip retention positioning arm lateral segment are positionably adjustable respective to one another along a longitudinal axis defined by each of the sheath interlock member engagement segment and the maxilla lip retention positioning arm lateral segment by retaining the sheath interlock member positioning surface and the maxilla lip lateral segment positioning surface against one another,
wherein the position retaining member is assembled on the interlock member engagement segment and the maxilla lip retention positioning arm lateral segment between the sheath interlock member riser segment and the lip retention section,
wherein when interlocked and installed, the tongue positioning and retention system retains the lip retention section in engagement with the individual's maxilla lip, maintaining the tongue embracing member in position, which maintains the individual's tongue in a desired position.

10. A tongue positioning and retention system as recited in claim 9, the position retaining member further comprising:
the body having an upper segment defining an interior upper surface,
a lower segment defining an interior lower surface, and
an intermediary segment joining the upper segment and the lower segment together,
wherein a distance between the interior upper surface and the interior lower surface defines a position retaining member internal span,
wherein the position retaining member internal span retains the sheath interlock member engagement segment and the maxilla lip retention positioning arm lateral segment in position respective to one another.

11. A tongue positioning and retention system as recited in claim 9,
wherein at least one of:
(a) the sheath interlock member engagement segment includes a wedge shaped feature, and
(b) the maxilla lip retention positioning arm lateral segment includes a wedge shaped feature.

12. A tongue positioning and retention system as recited in claim 11, wherein at least one of the sheath interlock member positioning surface and the maxilla lip lateral segment positioning surface include a friction enhancing surface texture.

13. A tongue positioning and retention system as recited in claim 11, wherein the sheath interlock member positioning surface and the maxilla lip lateral segment positioning surface include a friction enhancing surface texture each include interlocking mechanical features.

14. A tongue positioning and retention system as recited in claim 11, wherein the sheath interlock member positioning surface and the maxilla lip lateral segment positioning surface include a friction enhancing surface texture each include a series of interlocking projections and recessions.

15. A tongue positioning and retention system as recited in claim 11,
wherein the wedge shaped feature is formed having a smaller dimension and a larger dimension, the wedge shaped feature oriented locating the larger dimension closer to a free end and the smaller dimension being located closer to an attached end of the at least one of
(a) the sheath interlock member engagement segment and (b) the maxilla lip retention positioning arm lateral segment.

16. A tongue positioning and retention system, comprising:
a tongue embracing member comprising:
a sheath shaped to conform to a surface of a tongue of an individual, the sheath having a tongue receiving cavity defining an opening for receiving the individual's tongue provided at a proximal end thereof, the sheath having an orientation defined by a dorsal side and a ventral side, and
a sheath interlock member comprising a sheath interlock member riser segment extending upward from the dorsal side of the sheath, continuing with an interlock member engagement segment extending in a direction away from the opening for receiving the individual's tongue, the sheath interlock member engagement segment including a sheath interlock member positioning surface; and
a maxilla lip retention subassembly comprising:
a lip retention section having an arched shape, sized to follow a contour of a maxilla lip of the individual,
a maxilla lip retention positioning arm extending from the lip retention section, the maxilla lip retention positioning arm comprising a maxilla lip retention positioning arm lateral segment, the maxilla lip retention positioning arm lateral segment extending in a direction inward from a concave surface of the arched shape, the maxilla lip retention positioning arm lateral segment including a maxilla lip lateral segment positioning surface,
a position retaining member comprising:
a body having an upper segment defining an interior upper surface,
a lower segment defining an interior lower surface, and
an intermediary segment joining the upper segment and the lower segment together,
wherein a distance between the interior upper surface and the interior lower surface defines a position retaining member internal span,
at least one of (a) the sheath interlock member engagement segment and (b) the maxilla lip retention positioning arm lateral segment further comprising a wedge shaped feature,
wherein the sheath interlock member positioning surface and the maxilla lip lateral segment positioning surface are assembled contacting one another,
wherein the sheath interlock member engagement segment and the maxilla lip retention positioning arm lateral segment are positionably adjustable respective to one another along a longitudinal axis defined by each of the sheath interlock member engagement segment and the maxilla lip retention positioning arm lateral segment,
wherein a distance between the wedge shaped feature on one of the:
(a) the sheath interlock member engagement segment and
(b) the maxilla lip retention positioning arm lateral segment, and
a position retaining member engaging feature on the other of the:
(a) the sheath interlock member engagement segment and
(b) the maxilla lip retention positioning arm lateral segment
defines an adjustment control dimension that varies along a longitudinal length of an engaged combination of (a) the sheath interlock member engagement segment and (b) the maxilla lip retention positioning arm lateral segment,
wherein (a) sheath interlock member engagement segment and the maxilla lip retention positioning arm lateral segment are adjustable respective to one another when the position retaining member is located at a position where the adjustment control dimension is smaller than the position retaining member internal span and (b) the sheath interlock member engagement segment and the maxilla lip retention positioning arm lateral segment are fixed respective to one another when the position retaining member is located at a position where the adjustment control dimension is equal to or greater than the position retaining member internal span,
wherein the position retaining member is assembled on the interlock member engagement segment and the maxilla lip retention positioning arm lateral segment between the sheath interlock member riser segment and the lip retention section, wherein when interlocked and installed, the tongue positioning and retention system retains the lip retention section in engagement with the individual's maxilla lip, maintaining the tongue embracing member in position, which maintains the individual's tongue in a desired position.

17. A tongue positioning and retention system as recited in claim 16, wherein the wedge shaped feature is formed having a smaller dimension and a larger dimension, the wedge shaped feature oriented locating the larger dimension closer to a free end and the smaller dimension being located closer to an attached end of the at least one of (a) the sheath interlock member engagement segment and (b) the maxilla lip retention positioning arm lateral segment.

18. A tongue positioning and retention system as recited in claim 17, wherein at least one of the sheath interlock member positioning surface and the maxilla lip lateral segment positioning surface include a friction enhancing surface texture.

19. A tongue positioning and retention system as recited in claim 17, wherein the sheath interlock member positioning surface and the maxilla lip lateral segment positioning surface include a friction enhancing surface texture each include interlocking mechanical features.

20. A tongue positioning and retention system as recited in claim 17, wherein the sheath interlock member positioning surface and the maxilla lip lateral segment positioning surface include a friction enhancing surface texture each include a series of interlocking projections and recessions.

21. A tongue positioning and retention system as recited in claim 16, wherein the wedge shaped feature is provided as at least one of (a) a changing thickness of the sheath interlock member-positioning arm lateral arm segment and (b) a changing thickness of the maxilla lip retention positioning arm lateral segment.

22. A tongue positioning and retention system as recited in claim 21, wherein the position retaining member is fabricated having a tubular cross section shape.

23. A tongue positioning and retention system as recited in claim 16, wherein the position retaining member is fabricated having a tubular cross section shape.

* * * * *